US 9,874,526 B2

United States Patent
Liu et al.

(10) Patent No.: US 9,874,526 B2
(45) Date of Patent: Jan. 23, 2018

(54) METHODS AND APPARATUS FOR POLARIZED WAFER INSPECTION

(71) Applicant: KLA-Tencor Corporation, Milpitas, CA (US)

(72) Inventors: Sheng Liu, San Jose, CA (US); Guoheng Zhao, Palo Alto, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/468,608

(22) Filed: Mar. 24, 2017

(65) Prior Publication Data
US 2017/0276613 A1    Sep. 28, 2017

Related U.S. Application Data

(60) Provisional application No. 62/314,362, filed on Mar. 28, 2016.

(51) Int. Cl.
*G01N 21/88* (2006.01)
*G01N 21/21* (2006.01)
*G01N 21/95* (2006.01)

(52) U.S. Cl.
CPC ......... *G01N 21/8806* (2013.01); *G01N 21/21* (2013.01); *G01N 21/9501* (2013.01);
(Continued)

(58) Field of Classification Search
CPC . G01N 21/9501; G01N 21/21; G01N 21/8806
(Continued)

(56) References Cited

U.S. PATENT DOCUMENTS

| | | |
|---|---|---|
| 4,740,708 A | 4/1988 | Batchelder |
| 6,034,776 A | 3/2000 | Germer |

(Continued)

OTHER PUBLICATIONS

"PCT International Search Report—PCT/US2017/024326", dated Jul. 6, 2017, 3 pages.

(Continued)

*Primary Examiner* — Roy M Punnoose
(74) *Attorney, Agent, or Firm* — Kwan & Olynick, LLP

(57) ABSTRACT

Disclosed are methods and apparatus for inspecting a semiconductor sample. This system comprises an illumination optics subsystem for generating and directing an incident beam towards a defect on a surface of a wafer. The illumination optics subsystem includes a light source for generating the incident beam and one or more polarization components for adjusting a ratio and/or a phase difference for the incident beam's electric field components. The system further includes a collection optics subsystem for collecting scattered light from the defect and/or surface in response to the incident beam, and the collection optics subsystem comprises an adjustable aperture at the pupil plane, followed by a rotatable waveplate for adjusting a phase difference of electric field components of the collected scattered light, followed by a rotatable analyzer. The system also includes a controller that is configured for (i) selecting a polarization of the incident beam, (ii) obtaining a defect scattering map, (iii) obtaining a surface scattering map, and (iv) determining a configuration of the one or more polarization components, aperture mask, and rotatable ¼ waveplate, and analyzer based on analysis of the defect and surface scattering map so as to maximize a defect signal to noise ratio,

22 Claims, 17 Drawing Sheets

(52) U.S. Cl.
CPC .............. *G01N 2021/8848* (2013.01); *G01N 2201/0683* (2013.01)

(58) Field of Classification Search
USPC .................................. 356/364, 237.2, 237.5
See application file for complete search history.

(56) References Cited

U.S. PATENT DOCUMENTS

| | | | |
|---|---|---|---|
| 6,118,525 A | 9/2000 | Fossey et al. | |
| 6,924,893 B2* | 8/2005 | Oldenbourg | G02B 21/0004 356/369 |
| 7,710,564 B1 | 5/2010 | Hill et al. | |
| 8,891,079 B2* | 11/2014 | Zhao | G01N 21/9501 356/237.2 |
| 9,239,295 B2 | 1/2016 | Peng et al. | |
| 2004/0125373 A1* | 7/2004 | Oldenbourg | G02B 21/0004 356/364 |
| 2004/0125375 A1 | 7/2004 | Some | |
| 2011/0310382 A1* | 12/2011 | Uto | G01N 21/9501 356/237.2 |
| 2013/0114085 A1 | 5/2013 | Wang et al. | |
| 2013/0114880 A1 | 5/2013 | Matsumoto et al. | |
| 2013/0242294 A1* | 9/2013 | Taniguchi | G01N 21/956 356/237.5 |
| 2013/0265577 A1 | 10/2013 | Peng | |
| 2014/0009759 A1* | 1/2014 | Zhao | G01N 21/9501 356/369 |
| 2015/0069247 A1* | 3/2015 | Asundi | G01N 21/23 250/341.3 |

OTHER PUBLICATIONS

"PCT—Written Opinion—PCT/2017/024326", dated Jul. 6, 2017, 4 pages.

* cited by examiner

METHODS AND APPARATUS FOR POLARIZED WAFER INSPECTION

CROSS-REFERENCE TO RELATED APPLICATION

This application claims priority to U.S. Provisional Patent Application No. 62/314,362, filed 28 Mar. 2016, which application is incorporated herein by reference in its entirety for all purposes.

TECHNICAL FIELD OF THE INVENTION

The invention generally relates to the field of wafer inspection systems. More particularly the present invention relates to defect detection.

BACKGROUND

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the fabricated devices have become increasingly sensitive to defects. That is, defects which cause faults in the device are becoming increasingly smaller. The device needs to be generally fault free prior to shipment to the end users or customers.

Various inspection systems are used within the semiconductor industry to detect defects on a semiconductor wafer. However, there is a continued demand for improved semiconductor wafer inspection systems and techniques.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, an inspection system for inspecting a semiconductor sample is disclosed. This system comprises an illumination optics subsystem for generating and directing an incident beam towards a defect on the surface of a wafer. The illumination optics subsystem includes a light source for generating the incident beam and one or more polarization components for adjusting a ratio and/or phase difference between the two base vectors for the incident beam's electric field components. The system further includes a collection optics subsystem for collecting scattered light from the defect and/or surface in response to the incident beam, and the collection optics subsystem comprises an adjustable aperture at the pupil plane, followed by a rotatable waveplate for adjusting the phase difference for the collected scattered light's electric field components, followed by a rotatable analyzer. The system also includes a controller that is configured for (i) selecting a polarization of the incident beam, (ii) obtaining a defect scattering map, (iii) obtaining a surface scattering map, and (iv) determining a configuration of the one or more polarization components, aperture mask, and rotatable waveplate, and analyzer based on analysis of the defect and scattering map so as to maximize a defect signal to noise ratio.

In a specific implementation, the defect and surface scattering maps are obtained at four or more angles of the waveplate of the collection optics subsystem, and determining a configuration is accomplished by (i) for each pupil position at the pupil plane, determining defect Stokes parameters based on the obtained defect scattering map, (ii) for each pupil position at the pupil plane, determining surface Stokes parameters based on the obtained surface scattering map, (iii) generating a polarization orthogonality map based on the determined detect and surface Stokes parameters, and (iv) comparing relative polarization orthogonality values from the polarization orthogonality map and relative intensity distribution values from the defect scattering map to determine the configuration.

In one aspect, the one or more polarization components of the illumination subsystem include a rotatable ½ waveplate for controlling the incident beam's polarization angle and a rotatable ¼ waveplate for controlling the incident beam's circular or elliptical polarization. In a further aspect, the one or more polarization components of the illumination subsystem further comprise another ½ waveplate and a linear polarizer for controlling the incident beam's power and increasing a dynamic range. In yet a further aspect, the ¼ waveplate is positioned before the linear polarizer.

In another embodiment, the collection optics subsystem further includes an adjustable field stop for separately obtaining the defect and surface scattering maps. In another example, the collection optics subsystem further includes a sensor and one or more relay lens for relaying a pupil image to the sensor.

In another implementation, the illumination optics subsystem includes an aperture that is open to a full size and determining a configuration is accomplished by iteratively mathematically applying different settings for the aperture mask, ¼ waveplate, and analyzer so as to maximize the defect signal to noise ratio. In another aspect, a configuration of the aperture mask is determined so as to block areas of the pupil, except for areas with maximized polarization orthogonality and defect scattering intensity. In an alternative embodiment, the one or more polarization components of the illumination optics subsystem comprise a linear polarizer, and the rotatable waveplate of the collection optics subsystem is a rotatable ¼ waveplate. In another embodiment, the linear polarizer and the rotatable ¼ waveplate are each positioned at a conjugate plane. In yet another embodiment, the light source is a broadband light source, and the illumination optics subsystem is arranged to direct the incident beam through an objective onto the surface of the wafer.

In another embodiment, the invention pertains to a method of inspecting a semiconductor sample. The method includes (i) in an illumination optics subsystem of an inspection system, generating and directing an incident beam at a selected polarization state towards a defect on a surface of a wafer, wherein the illumination optics subsystem of the inspection system includes a light source for generating the incident beam and one or more polarization components for adjusting a ratio and/or phase difference for the incident beam's electric field components, (ii) in a collection optics subsystem of an inspection system, collecting scattered light from the defect and/or surface in response to the incident beam, wherein the collection optics subsystem of the inspection system comprises an adjustable aperture at the pupil plane, followed by a rotatable waveplate for adjusting a phase difference of electric field components of the collected scattered light, followed by a rotatable analyzer, (iii) obtaining a defect scattering map based on the collected scattered light, (iv) obtaining a surface scattering map based on the collected scattered light, and (v) determining a configuration of the one or more polarization components, aperture mask, and rotatable waveplate, and analyzer based on analysis of the defect and surface scattering map so as to maximize a defect signal to noise ratio.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with these specific embodiments, it will be understood that it is not intended to limit the invention to these embodiments.

Certain inspection system embodiments are described herein as being configured for inspecting semiconductor structures. Other types of structures, such as solar panel structures, optical disks, etc., may also be inspected or imaged using the inspection apparatus of the present invention.

A semiconductor wafer inspection can sometimes use an inspection tool that is configurable to have a linearly polarized light configuration, such as an S or P polarization setting. Selection of either S or P polarization can be based on the wafer type, defect type (e.g., particle), etc.

One form of inspection microscopy that utilizes S and P polarization is a laser dark field (DF) microscope, which has been widely used in the wafer inspection industry to detect nanoscale anomalies on semiconductor wafers. The DF technique often enhances defect detection sensitivity by blocking specular reflection from the wafer while collecting mostly scattered light. In addition, an illumination polarizer, analyzer, aperture mask, and Fourier filter can be applied to further improve sensitivity. Among these applied factors, illumination polarization is normally considered to have the most direct impact on detect sensitivity. Other types of systems, such as a polarized broadband system, may also utilize circularly, S, and, P configurations.

In general, P polarization illumination is more sensitive for smaller defects on smooth surfaces, such as described in U.S. Pat. No. 6,118,525 by Fossey et al. Furthermore, a linear polarizer together with a corresponding mask could be applied to null optical scattering from wafers to thereby enhance defect sensitivity, such as described in U.S. Pat. No. 8,891,079 by Zhao et al., which patent is incorporated herein by reference.

Figure 1A:
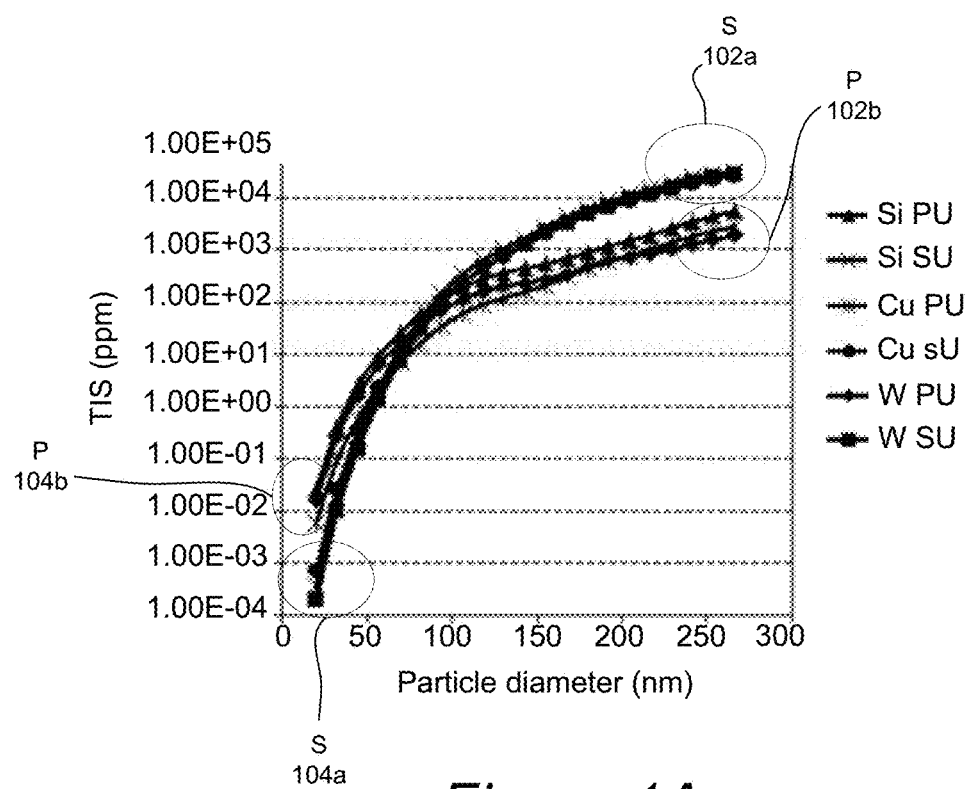
FIG. 1A is a graph of the Total Integral Scattering (TIS) under S and P illumination as a function of defect size and different defect materials.
Figure 1B:
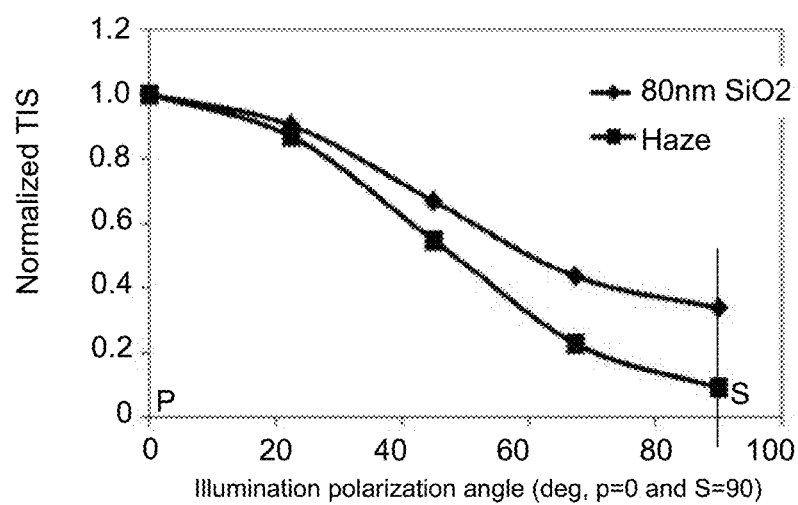
FIG. 1B is a graph of normalized TIS as a function of illumination polarization angle.

FIG. 1A illustrates that, as particle diameter increases above approximately 80 nm, the Total Integral Scattering (TIS) under S illumination exceeds the TIS under P illumination. This TIS difference results in better detection sensitivity for larger size defects. That is, the S polarization results in a much larger TIS (e.g., 102a) for defects sizes that are about 80 nm and greater, as compared to the TIS for P polarization 102b). In contrast, for smaller defects the TIS for P polarization (e.g., 104b) is lower than the TIS for S polarization (e.g., 104a). FIG. 1B is a graph of normalized TIS as a function of illumination polarization angle. As shown, an S illumination results in a wider difference between an 80 nm defect and haze.

Although selection of either S or P for smaller vs. larger defects works well under some conditions, there are other effects that may make this choice less clear for maximizing defect sensitivity. For example, P illumination has differently aligned polarization vectors for an 80 nm. SiO2 particle defect and the water substrate, resulting in better defect signal to noise ratio (SNR) for an 80 nm defect. In contrast, polarization vectors of an 80 nm defect and wafer substrate are mostly aligned under S illumination, leaving little room for further improvement of defect signal to noise ratio by excluding wafer surface scattering using a polarizer.

Circular polarization illumination is a polarization state that is the superposition of P and S polarizations with equal amplitude and a constant phase offset of $\pi/2$. Said in another way, circular polarization can be viewed as an average of P and S illumination with a fixed phase offset. A circular polarization finds limited application, as compared to either P or S illumination, as further described in U.S. Pat. No. 4,740,708 by Batchelder.

In certain cases, either P or S polarization yields a better sensitivity. However, an improved result may occur if one were to account for both the scattering intensity and the polarization orthogonality between defects and wafer substrates. Qualitatively, polarization orthogonality is a measure of how much defect and wafer surface scatterings may be separated optically based on the difference in their polarization states. As an example, if both particle and wafer scatterings are linearly polarized and, additionally, if one is P polarized while the other is S polarized, their polarization orthogonality can be defined as 1. In this case, wafer scattering could be fully extinguished by a linear polarizer while the other particle signal remains unchanged. In contrast, if both scatterings are linearly polarized but parallel to each other, their polarization orthogonality can be defined as 0. In this latter case, there is no means to differentiate the two with a polarizer. Furthermore, if particle scattering is linearly polarized while wafer scattering is circularly polarized, their polarization orthogonality can be defined as 0.5 in that a linear analyzer can be aligned with the polarization direction of particle scattering while reducing the wafer scattering by 2×.

To quantitatively describe the polarization orthogonality, the E field of purely polarized light can be first defined by a Jones vector:

$$\vec{E} = \begin{bmatrix} E_x \\ E_y \end{bmatrix} = \begin{bmatrix} a_x e^{i\varphi_x} \\ a_y e^{i\varphi_y} \end{bmatrix} \quad (1)$$

where $a_x$ and $a_y$ are the amplitudes of the x and y components of the electric field, and $\varphi_x$ and $\varphi_y$ are the phase of the x and y components. Only the phase difference $\delta = \varphi_y - \varphi_x$ is needed to fully define a polarization state.

The following Table 1 gives six examples of normalized Jones vectors.

TABLE 1

| Polarization | Corresponding Jones vector |
|---|---|
| Linear polarized in the x-direction (horizontal) | $\begin{pmatrix} 1 \\ 0 \end{pmatrix}$ |
| Linear polarized in the y-direction (vertical) | $\begin{pmatrix} 0 \\ 1 \end{pmatrix}$ |
| Linear polarized at 45° from the x-direction (diagonal) | $\begin{pmatrix} 1 \\ 1 \end{pmatrix}$ |
| Linear polarized at −45° from the x-direction (anti-diagonal) | $\begin{pmatrix} 1 \\ -1 \end{pmatrix}$ |
| Right hand circular polarized (RCP or RHCP) | $\begin{pmatrix} 1 \\ -i \end{pmatrix}$ |
| Left hand circular polarized (LCP or LHCP) | $\begin{pmatrix} 1 \\ +i \end{pmatrix}$ |

The polarization orthogonality of two polarized E fields, which include one for defect (also referred to herein as "particle") scattering and one for wafer (also referred to herein as 'surface") scattering, may be defined as:

$$Polorth = 1 - \frac{|\vec{E}_{par}\vec{E}_{wafer}^*|}{|\vec{E}_{par}||\vec{E}_{wafer}^*|} = 1 - \frac{\left| a_{par\_x} a_{wafer\_x} e^{i(\phi_{par\_x} - \phi_{wafer\_x})} + a_{par\_y} a_{wafer\_y} e^{i(\phi_{par\_y} - i\phi_{wafer\_y})} \right|}{\sqrt{a_{par\_x}^2 + a_{par\_y}^2} \sqrt{a_{wafer\_x}^2 + a_{wafer\_y}^2}} \quad (2)$$

The mathematical definition above could be interpreted as 1 minus the normalized magnitude of one E field vector projected onto the other E field vector. By definition, the values of Polorth are from 0 to 1, with 0 meaning that two polarization states are identical and 1 meaning completely orthogonal. Under ideal conditions in which wafer scattering is the dominate noise source, maximizing polarization orthogonality generally leads to the most optimum SNR.

For rougher surfaces such as some metal film wafers, the scattered light can be partially polarized. In this case, the partially polarized scattered light can be separated into two parts of purely polarized light and un-polarized light and treated separately. Partially polarized light can be defined by Stokes vector as given by:

$$S = \begin{bmatrix} S_0 \\ S_1 \\ S_2 \\ S_3 \end{bmatrix} \quad (3)$$

where $S_{0,1,2,3}$ are the four elements of the Stokes vector which can be extracted from polarimetry measurements. The intensity of the polarized portion is given by:

$$S_{pol} = \sqrt{S_1^2 + S_2^2 + S_3^2} \quad (4)$$

and the intensity of unpolarized light is given by:

$$S_{unpol} = S_0 - S_{pol} \quad (5)$$

The degree of polarization is given by:

$$P = \frac{S_{pol}}{S_0} \quad (6)$$

The x and y components of polarized light is given by:

$$|E_x|^2 = \frac{1}{2}(S_{pol} + S_1) \quad (7)$$

$$|E_y|^2 = \frac{1}{2}(S_{pol} - S_1)$$

The phase difference between x/y components of the polarized portion of the E field is expressed as:

$$\tan \delta = \frac{S_3}{S_2} \quad (8)$$

By definition, the phase difference between the x/y component of the unpolarized portion of the E field is randomly distributed between 0 to 360 degrees.

For wafer inspection use cases, particle sizes are generally small enough such that the scatted light from particles is always polarized. Therefore, only the wafer surface scattering is sometimes partially polarized. The polarized portion of wafer scattering can be treated as discussed previously, and the unpolarized portion of wafer scattering will typically be suppressed by half for any combination of waveplate and analyzer in the collection path. The un-suppressed part of the unpolarized light of wafer scattering represents a residual background that may be taken into account in an SNR optimization process. The degree of polarization is also dependent on pupil location, which further complicates the SNR optimization process. In this case, optimization may be based on Stokes vector propagation through the polarizing components. SNR can be written as:

$$SNR_{inc\,pol} \propto \frac{\int_{pupil\,mask} S_{0\_par}^{out} dA}{\int_{pupil\,mask} S_{0\_wafer}^{out} dA} \quad (9)$$

$$S_{par}^{out} = M_W M_A S_{par}$$

$$S_{wafer}^{out} = M_W M_A S_{wafer}$$

where and $S_{0\_par}^{out}$ are $S_{0\_wafer}^{out}$ the first elements of the Stokes vectors of $S_{par}^{out}$ and $\bar{S}_{par}^{out}$, which are the intensity of particle scattering and wafer scattering after passing through waveplate and analyzer. $M_W$ is the Mueller matrix of the waveplate and $M_A$ is the Mueller matrix of the analyzer.

Certain embodiments of the present invention pertain to inspection systems that utilize illumination polarization angles that are intermediate between the S and P polarization states to improve defect detection sensitivity. Under different inspection and specimen conditions, a specific intermediate polarization angle can be selected to minimize noise and improve defect SNR and, thereby, improve defect detection sensitivity.

Figure 2:
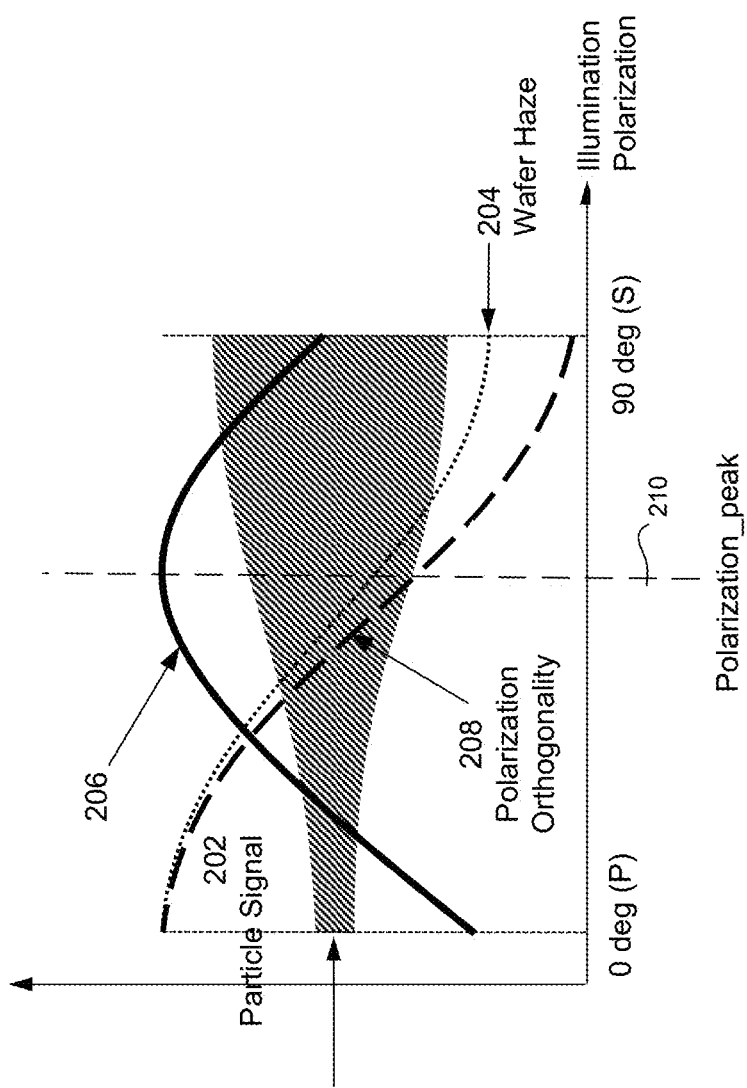
FIG. 2 is a graph showing how various parameters change as a function of the incidence linear polarization angle and how they can cohesively affect the defect SNR and selection of the illumination polarization angle.

All parameters in the above SNR Equation (9) are a function of input polarization angle. It can be demonstrated that, for some medium roughness surfaces, there is an optimum illumination polarization angle between pure P and S polarization because the illumination polarization angle affects particle scattering, surface scattering, and polarization orthogonality at different rates. Thus, an optimum illumination polarization between S and P can be found and used. In these optimum illumination polarization embodiments, phase retardation can be compensated by using a ¼ waveplate, and a polarizer can be used to suppress surface scattering after it is linearized by the phase plate, FIG. 2 is a graph showing how various signal parameters change as a function of the incidence linear polarization angle and how they can cohesively affect the defect SNR and selection of the illumination polarization angle. The horizontal axis of FIG. 2 indicates the linear incidence polarization angle. An illumination angle of 0 degrees corresponds to P polarization (E field parallel to plane of incidence) and 90 degrees corresponds to S polarization (E field perpendicular to plane of incidence).

Figure 3A:
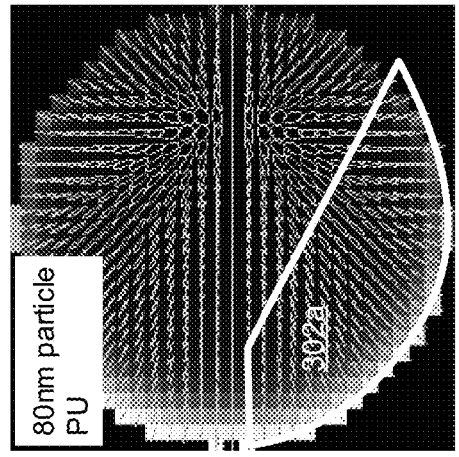
FIG. 3A depicts the alignment of polarization vectors for an 80 nm SiO2. particle defect for a P polarization illumination.
Figure 3B:
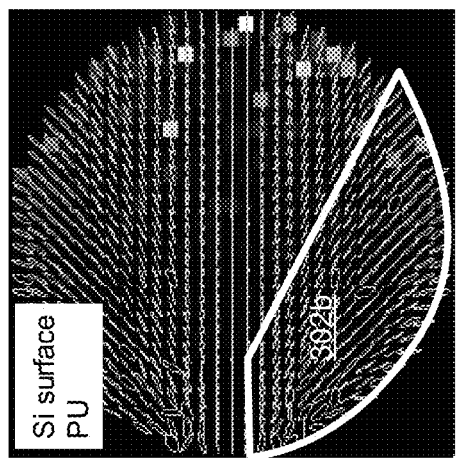
FIG. 3B depicts the alignment of polarization vectors for a silicon water substrate for a P polarization illumination.
Figure 3C:
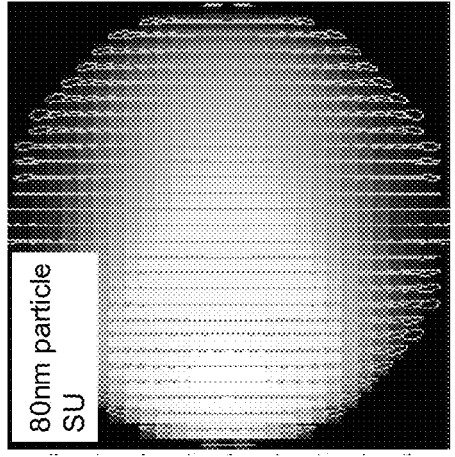
FIG. 3C depicts the alignment of polarization vectors for an 80 nm SiO2 particle defect for an S polarization illumination.
Figure 3D:
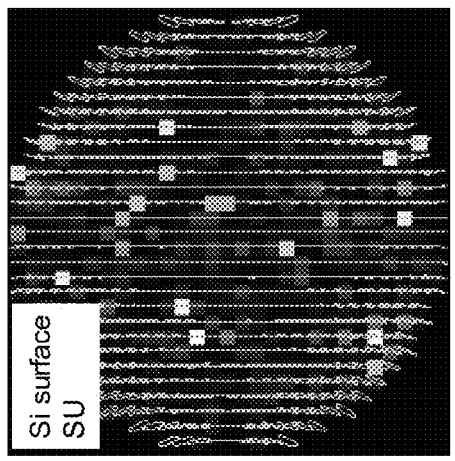
FIG. 3D depicts the alignment of polarization vectors for a silicon wafer substrate for an S polarization illumination.

As shown in FIGS. 3A-B, polarization orthogonality under P polarization is high towards forward edge portions of the pupil (302a and 302b). In contrast, polarization orthogonality is low under S polarization throughout the entire pupil as shown in FIGS. 3C-D. This effect indicates, as illumination polarization changes from S to P, that polarization orthogonality gradually increases as illustrated by the thick dashed line in FIG. 2, which is labeled from S on the far right of the horizontal axis to P on the far left and at the origin of this axis.

Additionally, in FIG. 2, the defect SNR (206) is proportional to defect signal divided by total wafer haze, and then multiplied by a polarization orthogonality factor. The more orthogonality there is between defect and wafer scattering polarization implies a higher probability that defect signal could be separated from wafer signal by an optical analyzer. Accordingly, the polarization orthogonality may have an optimum value (210), which is an intermediate polarization state between S and P, and which results in a SNR peak (on curve 206), which also corresponds to maximized defect sensitivity.

Figure 4:
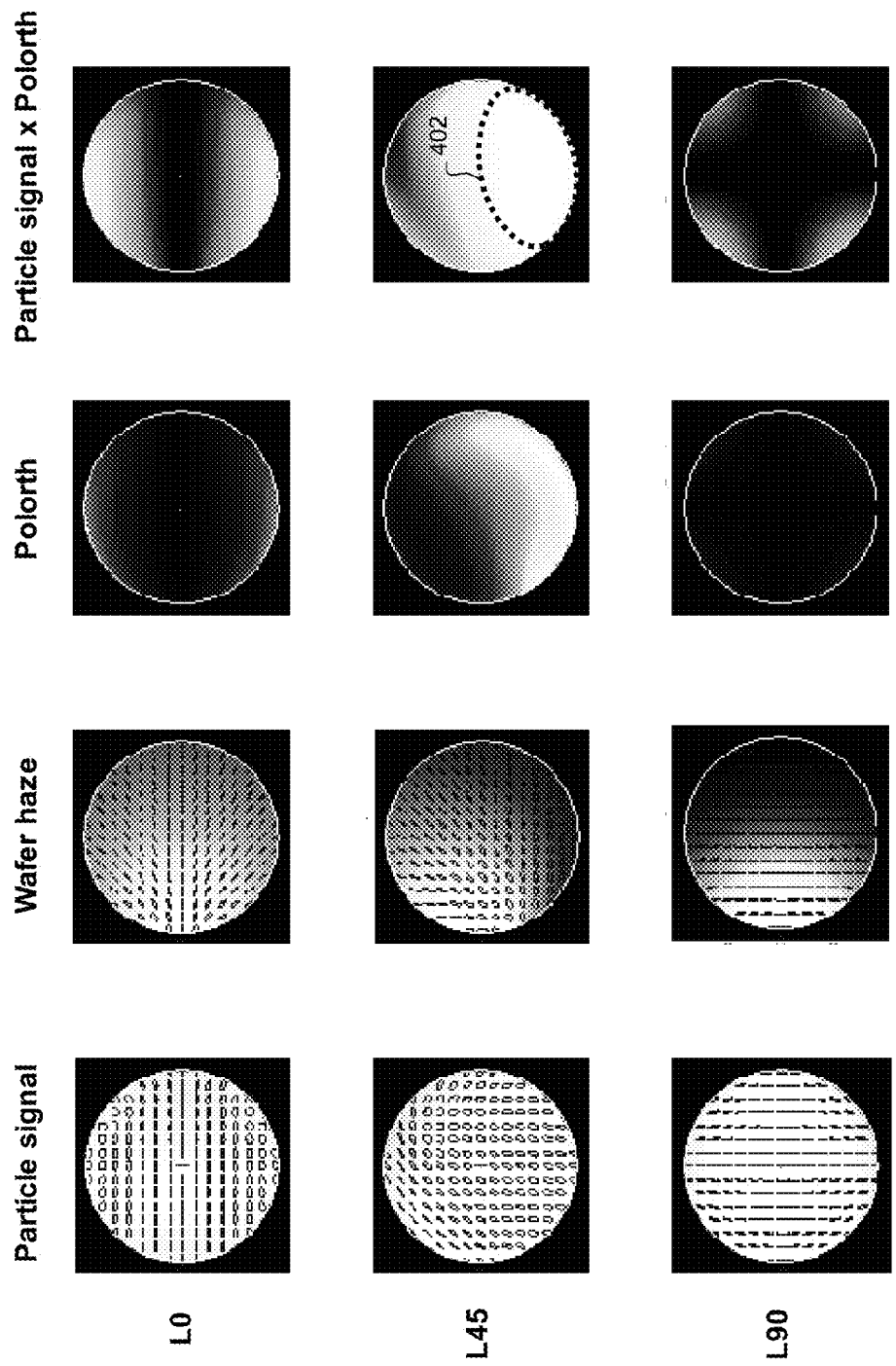
FIG. 4 illustrates the results of a set of numerical simulations based on an 80 nm $SiO_2$ particle defect on a rough seed Cu wafer.

FIG. 4 illustrates the results of a set of numerical simulations based on an 80 nm SiO$_2$ particle defect on a rough seed Cu wafer. Both the particle scattering and wafer scattering are shown at three linear incidence polarization status, L0(P), L90(S) and L45, where L45 means the incident light is linearly polarized and its polarization angle is 45-degrees relative to L0(P) and L90(S). The corresponding polarization orthogonality maps are plotted at the 3rd column of FIG. 4. Increasing brightness levels represent increasing polarization orthogonality values (white being highest). Thus, L45 apparently maximizes polarization orthogonality particularly towards the bottom half of the pupil. In the 4th column of FIG. 4, the particle signal multiplied by the polarization orthogonality factor is plotted since it is desirable to also consider the relative intensity of the particle signal. In general, the linear incidence polarization of L45 has a better defect sensitivity compared to either pure S or P illumination polarization. In addition, the simulation results indicate that a mask applied towards the bottom half of the pupil (encircled by the thick dotted line 402) could further enhance defect sensitivity. These simulations show that an intermediate polarization state near L45 could maximize defect sensitivity.

Figure 5:
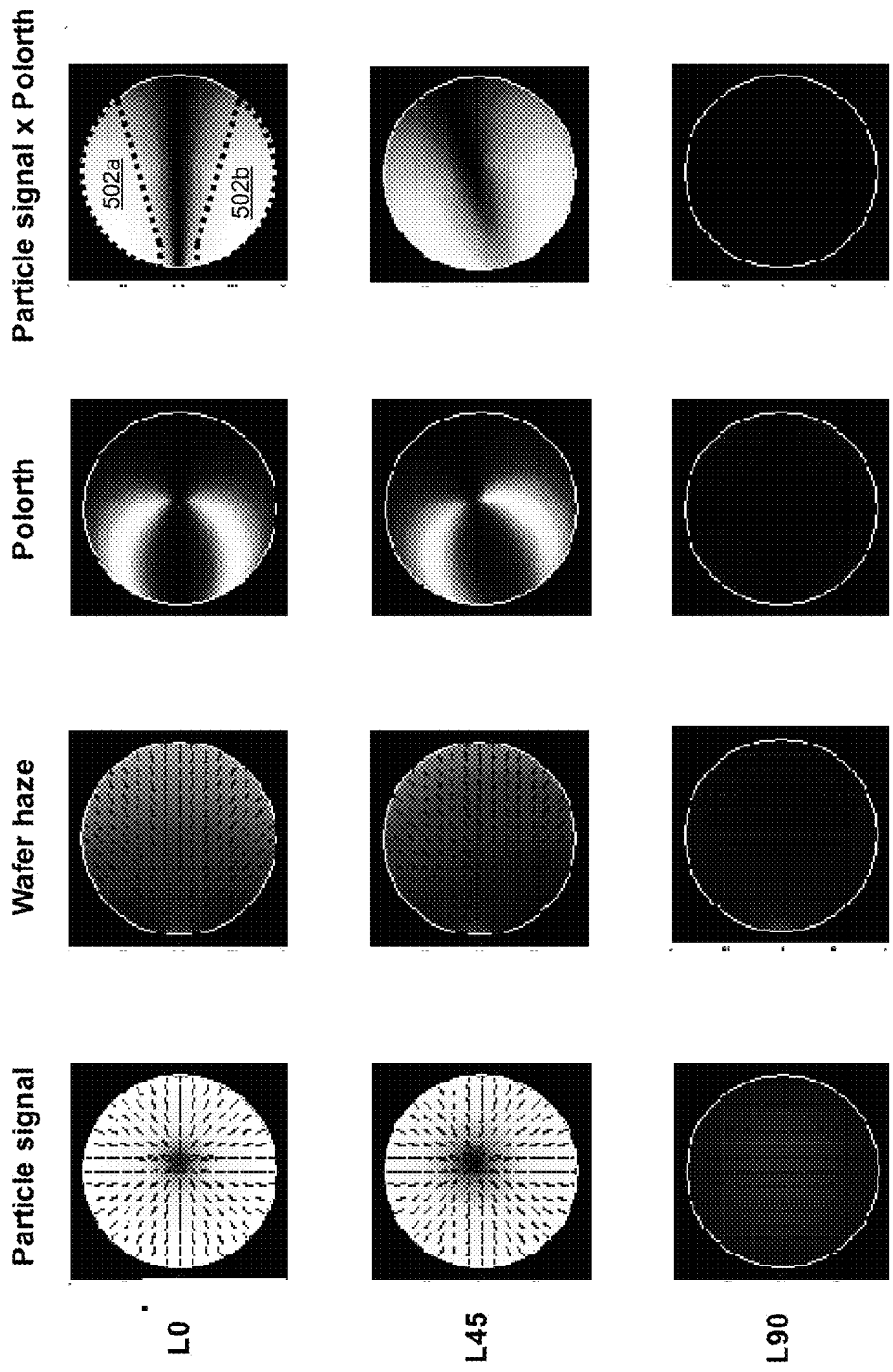
FIG. 5 shows simulation results of 20 nm SiO2 particle defect scattering on a smooth bare Si wafer.

It is worth to note that optimization of incidence polarization may not work for all cases. For instance, FIG. 5 shows simulations of 20 nm SiO2 particle defect scattering on a smooth bare Si wafer. As incidence polarization changes from L0(P) to L90(S), both particle signal and wafer haze decreases while particle signal drops at a faster rate. Meanwhile polarization orthogonality monotonically decreases towards L90. This means that the best case is to apply an analyzer at L0(P), as disclosed in U.S. Pat. No. 8,891,079 B2 by Zhao et al., instead of at an intermediate polarization status. In addition, the simulation results indicate that a mask applied towards certain portions of the pupil (two areas 502a and 502b encircled by the thick dotted lines) could further enhance defect sensitivity.

One of the advantages of the above SNR optimization process is that, as long as defect scattering and wafer scattering properties at the pupil can be extracted, the optimization pipeline is unrelated to which type of waveplate or analyzer is applied. Alternatively speaking, polarization orthogonality is an intrinsic parameter determined solely by the defect and wafer scattering properties.

While in reality for different wafer and defect types, it is an overwhelmingly challenging task to accurately predict how the optical scattering behaves under different illumination polarization states. When little information is known for both defect size and wafer structures, it is merely possible to retrieve some information from numerical simulations. A relatively practical approach is to measure the full scattering maps of both wafer and defect areas of interest at any given illumination polarization state.

To summarize, illumination polarization may be fully optimized at states between P and S states, including states other than P, S, or circular polarization, in addition to optimized collection masks, waveplates, and analyzers. Such combination may additionally offer supplementary improvement of SNR, as compared to strict P and S systems.

Any suitable tool may be utilized, as long as variable polarization states that are between S and P polarization states may be setup on the tool. The selectable polarization states include S and P polarization states, as well as states that are not S or P polarization. In general, an applicable inspection tool for implementation of techniques of the present invention may include at least one light source for generating an incident light beam at different polarization states. Such an inspection may also include illumination optics for directing the incident beam to the area-of-interest, collection optics for directing scattered electromagnetic waveforms (e.g., scattered light, X-rays, etc.) from the area-of-interest in response to the incident beam, a sensor for detecting this scattered output and generating an image or signal from the detected scattered output, and a controller or computer subsystem for controlling the components of the inspection tool and facilitating defect detection in various materials and structures as described further herein.

Figure 6:
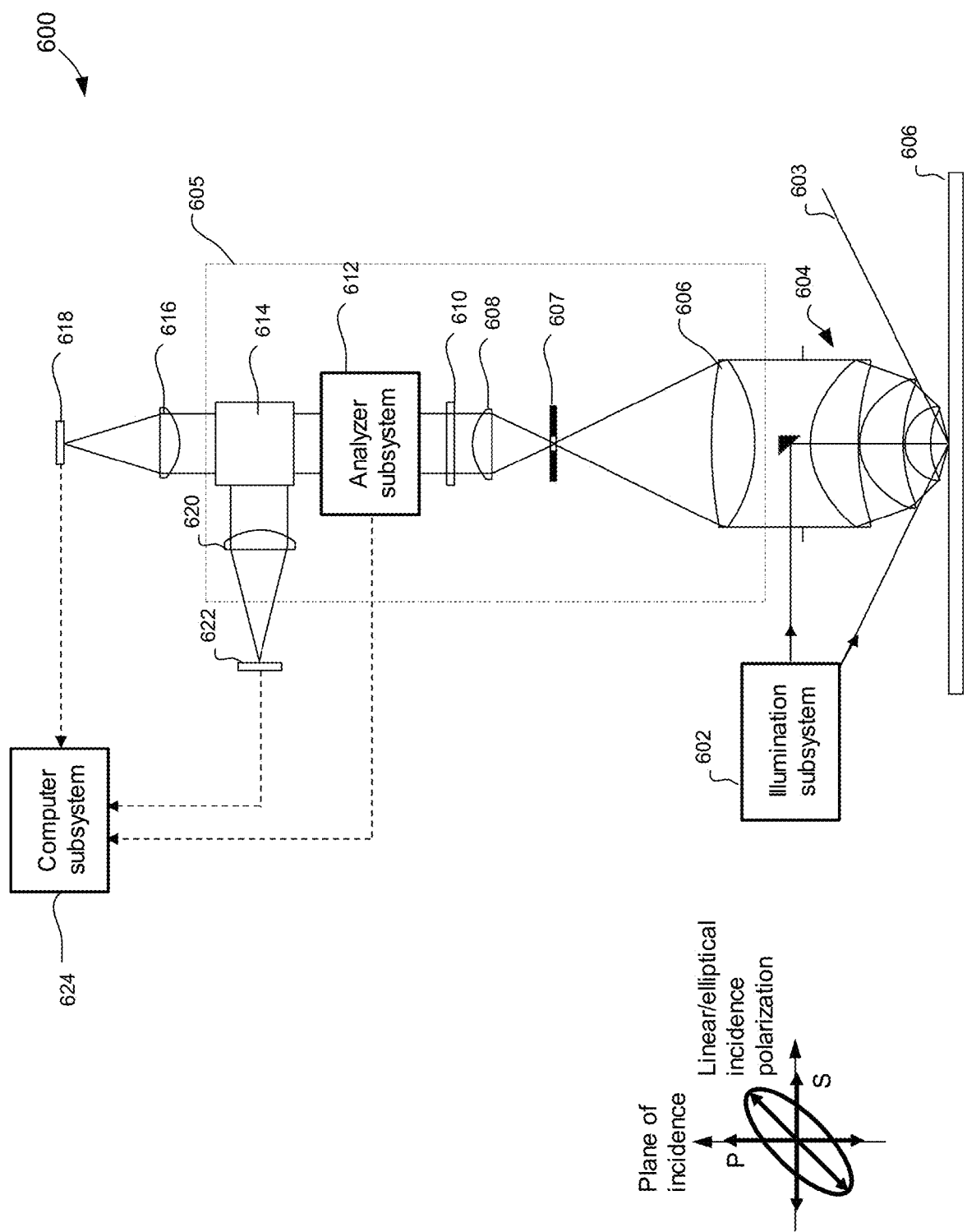
FIG. 6 is a diagrammatic representation of an inspection system in accordance with one embodiment of the present invention.

FIG. 6 is a diagrammatic representation of an inspection system 600 in accordance with one embodiment of the present invention. As shown, the system includes an illumination subsystem 602 for generating an incident beam (e.g., any suitable electromagnetic waveform) and directing such beam towards an objective system 604 and then towards a sample 606, such as a wafer. The illumination subsystem 602 may also be configured to control the incidence polarization state onto the sample 606.

Examples of light sources for generating the incident beam include a laser-driven light source, a high-power plasma light source, a transillumination light source (e.g., halogen or Xe lamp), a filtered lamp, LED light sources, etc. The inspection system may include any suitable number and type of additional light sources, including broadband light sources.

The incident beam from the light source may generally pass through any number and type of lenses which serve to relay (e.g., shape, focus or adjust focus offset, filter/select wavelengths, filter/select polarization states, resize, magnify, reduce distortion, etc.) the beam towards a sample. For instance, the illumination module 602 may also include any number of linear polarizers and waveplates as described further herein.

In response to the incident beam impinging on the sample, scattered light may then be received and directed by a collection system 605 towards one or more sensors (e.g., 622 and 618). The objective system 604 collects scattered light from the water. The collection system 605 may include any suitable number and type of optical components, such as aperture or field stop 607, collimator 608, aperture mask 610, analyzer subsystem 612, splitter 614, and focus lens 616 and 620 for focusing the scattered light towards respective detectors 618 and 622. A magnified image of wafer is formed on the image sensor at back end of collection path. By way of example, each detector may be in the form of a CCD (charge coupled device) or TDI (time delay integration) detector, photomultiplier tube (PMT), or other sensor.

Analyzer subsystem 612 generally includes multiple optical elements for analyzing scattered light and optimizing defect sensitivity, in conjunction with the illumination subsystem 602 being optimized to a selected illumination polarization. Malus' law, which is named after Etienne-Louis Malus, says that when a perfect polarizer is placed in a polarized beam of light, the intensity, I, of the light that passes through is given by:

$$I = I_0 \cos^2 \theta_i,$$

where $I_0$ is the initial intensity, and $\theta_i$ is the angle between the light's initial polarization direction and the axis of the polarizer. In general, a beam of unpolarized light can be thought of as containing a uniform mixture of linear polarizations at all possible angles. Since the average value of $\cos^2 \theta$ is ½, the average transmission coefficient becomes:

$$I/I_0 = 1/2$$

If two polarizers are placed one after another (the second polarizer is generally called an analyzer), the mutual angle between their polarizing axes gives the value of $\theta$ in Malus' law. If the two axes are orthogonal, the polarizers are crossed and, in theory, no light is transmitted.

A computer subsystem is connected to both illumination subsystem and analyzer subsystem for automated control. For instance, the signals captured by each detector can be processed by computer subsystem 624, which may include a signal processing device having an analog-to-digital converter configured to convert analog signals from each sensor into digital signals for processing. The computer subsystem 624 may be configured to analyze intensity, phase, and/or other characteristics of the sensed light beam. The computer subsystem 624 may be configured (e.g., with programming instructions) to provide a user interface (e.g., on a computer screen) for displaying resultant images and other inspection characteristics as described further herein. The computer subsystem 624 may also include one or more input devices (e.g., a keyboard, mouse, joystick) for providing user input (e.g., as changing wavelength, polarization, mask configuration, aperture configuration, etc.), viewing detection results data or images, setting up an inspection tool recipe, etc.

The computer subsystem 624 may be any suitable combination of software and hardware and is generally configured to control various components or other controllers of the inspection system. The computer subsystem 624 may control selective activation of the illumination source, the illumination or output aperture settings, wavelength band, focus offset setting, polarization settings, analyzer settings, etc. The computer subsystem 624 may also be configured to receive images or signals generated by each detector and analyze the resulting images or signals to determine whether defects are present on the sample, characterize defects present on the sample, or otherwise characterize the sample. For example, the computer subsystem 624 may include a processor, memory, and other computer peripherals that are programmed to implement instructions of the method embodiments of the present invention. The computer subsystem 624 may also have one or more processors coupled to input/output ports, and one or more memories via appropriate buses or other communication mechanisms.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

System embodiments of the present invention described herein can be used to characterize optical scattering intensity and polarization states of defects and wafer background while also optimizing the illumination polarization, in conjunction with optimizing the collection aperture mask, waveplate and analyzer. Compared to prior architectures with only P, S, or circular illumination polarization, embodiments of the present invention improve defect sensitivity on both opaque rough film wafers and pattern wafers. When configured to characterize optical scattering from wafers, system embodiments of the present invention can provide a polarimetry scatterometer capable of capturing high dynamic range (HDR) Stokes vector maps of scattered light at the pupil plane of the microscope objective. Adopting different field stops and aperture masks, both the intensity distribution and polarization status of scattered light from a defect and wafer can be extracted, which later can assist defect sensitivity optimization.

When customized to improve defect sensitivity, certain embodiments of the present invention are configurable to output an arbitrary illumination polarization state while simultaneously optimizing the collection mask and analyzer, so as to find an optimal combination of configurable variables of the optical system as further described herein. Bench test results show 1.6× to 4× improvement of SNR of deposited SiO2 particle defects on opaque film wafers and 1.7× SNR improvement of protrusion defects on line pattern wafers, compared to conventionally optimal imaging modes as baselines.

Figure 7:
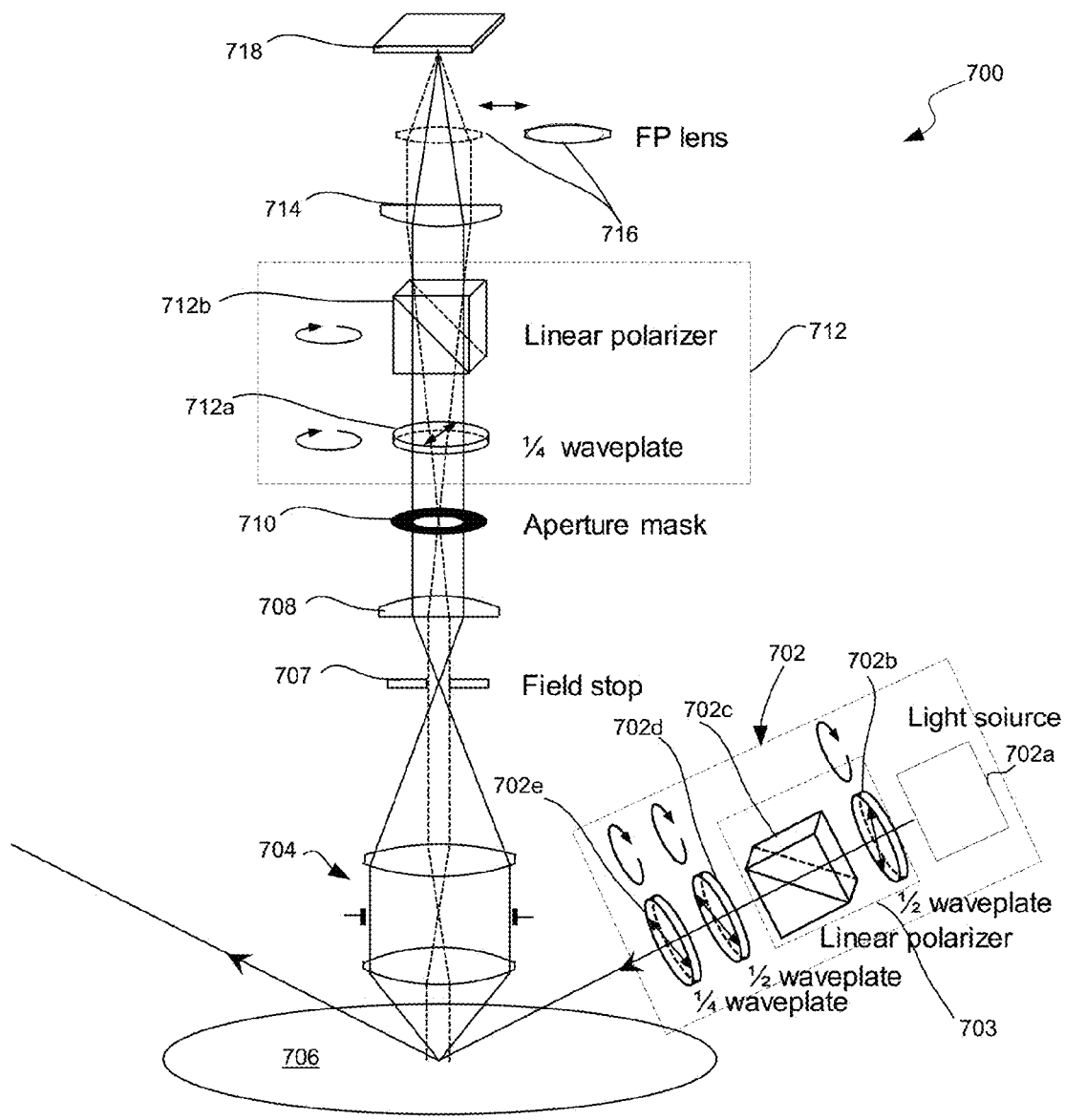
FIG. 7 shows detailed schematics of one possible implementation of an inspection apparatus in accordance with a specific embodiment of the present invention.

FIG. 7 shows detailed schematics of one possible implementation of an inspection apparatus 700 in accordance with one embodiment of the present invention. This inspection system has an S-to-P variable polarization range for illumination and collection. Similarly to the system of FIG. 6, a dark field microscope objective 704 may be employed to collect scattered light from the sample. For a polarimetric scatterometry characterization application, the objective lens may have these four features: 1) high numerical aperture (NA) imaging (e.g., greater than about NA 0.9) enabling collection of as much scattered light as possible towards higher spatial frequency, 2) polarization states of scattered light is generally preserved, 3) an accessible pupil plane at which an analyzer and mask are located, and 4) an accessible field plane at which configurable field stops could be inserted.

The illumination subsystem 702 shown in FIG. 7 may include a light source 702a along with four polarization elements: a first ½ waveplate 702b, a linear polarizer 702c, a second ½ waveplate 702d, and a ¼ waveplate 702e. The illumination subsystem 702 is generally configurable and freely manipulated so as to produce illumination polarization status other than a P, S, or circular state. More generally, the illumination optics subsystem may include one or more polarization components for adjusting a ratio and/or phase difference for the incident beam's electric field components.

The illumination subsystem 702 may include any suitable components, optical or otherwise, to control power. In the illustrated embodiment, the linear polarizer 702c has a fixed position to extinguish polarization in every direction, except in one linear direction. The first rotatable ½ waveplate 702b shifts the direction of the linearly polarized light that is received from the linear polarizer 702c. The combination of the first rotatable ½ waveplate 702b and linear polarizer 702c controls incidence power and increases dynamic range of the system. The illumination subsystem may also include one or more polarization components for introducing a polarization state in the incident beam that is between S and P states. The ½ waveplate 702b serves to rotate the incident light's polarization direction by 0 to 180 degrees without a change in intensity, while the linear polarizer 702c extinguishes polarized light and controls incidence power. Any other suitable components for controlling power and/or increasing the dynamic range may be utilized in place of ½ waveplate and linear polarizer combination.

Figure 8:
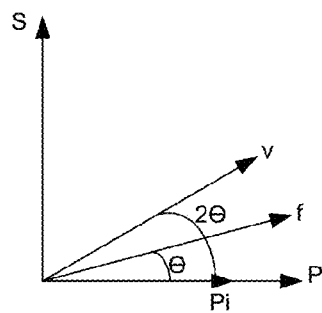
FIG. 8 is a diagrammatic representation of adjustment of an incident polarization direction in accordance with one embodiment of the present invention.

The rotatable second ½ waveplate 702d generally controls the incidence light's linear polarization angle, and the rotatable ¼ waveplate 70e controls the degree of elliptical polarization. Specifically, the addition of the second rotatable ½ waveplate 702d in a position after the linear polarizer provides a mechanism to continuously adjust the polarization angle to values between S and P. More specifically, the polarization angle will be 2θ, which is twice the angle between the incident polarization angle and the fast axis of the ½ waveplate 702d. Thus, the ½ waveplate 702d is rotated to a position that is ½ the desired rotation for the polarization. As illustrated by an example shown in FIG. 8, the incident polarization (Pi), which is oriented in a P polarization direction, is rotated by 2θ to result in vector v when a ½ waveplate is positioned at angle θ. Referring to the example of FIG. 2, the $2^{nd}$ ½ waveplate 702d would be rotated to produce a polarization 210 that corresponds to the maximum particle signal 206 (and a significantly lower wafer signal 204).

The ¼ waveplate 702e can be used and positioned to change the phase of the incident light. For instance, the ¼ waveplate 702e is positioned to generate circular or eliptical polarized incident light. This ¼ waveplate 702e is optional.

Along the collection path sequence, a collection subsystem includes a full field stop 707, a collimator 708, an aperture mask 710 at a conjugate pupil plane, a rotatable ¼ waveplate 712a, a rotatable linear polarizer (or analyzer) 712b, relay lens 714, Fourier plane (FP) lens 716, and an image sensor 718. Both the field stop 707 and the aperture mask 710 may be adjustable so that an area of the pupil plane that is more sensitive to wafer scattering, as compared with background scattering, reaches a sensor 718. Both the ¼ waveplate 712a and linear polarizer 712b, as well as the FP lens, may be slidably positioned in and out of the optical path for flexible control of scattered light from the sample 706.

Figure 9A:
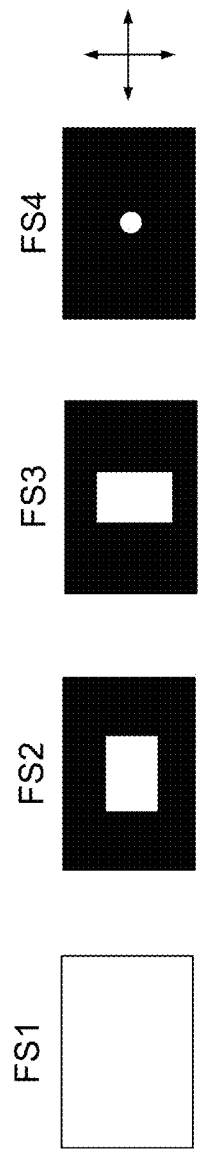
FIG. 9A shows a plurality of differently sized field stop configurations.
Figure 9B:
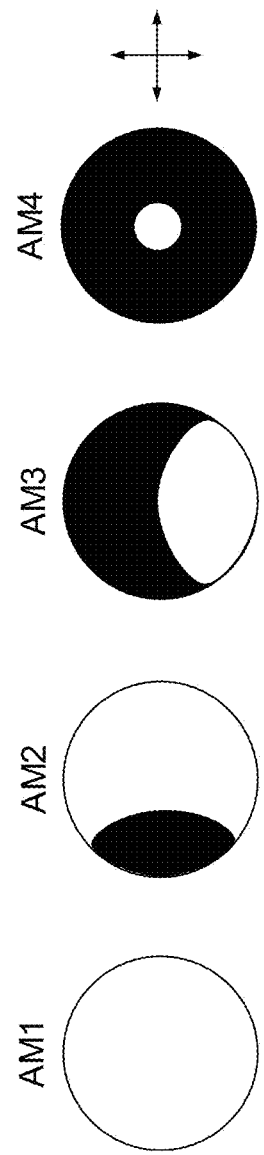
FIG. 9B shows a plurality of differently sized aperture mask configurations.

While the system is configured for scatterometry measurements, for example, a full size field stop and a full size aperture mask can be used. FIG. 9A shows a plurality of differently sized field stop configurations FS1, FS2, FS3, and FS4, while FIG. 9B shows a plurality of differently sized aperture mask configurations AM1, AM2, AM3, and AM4. The full size field stop is labelled ESL while the full size aperture mask is labeled AM1.

In some examples, the light reflected and scattered from a perfectly flat surface (e.g., mirror) tends to not have a phase shift so that the scattered and reflected light has correlated phase, which results in linear or elliptical/circular polarized wafer scattered light. In other cases, different parts of the wafer scattering can be both unpolarized and polarized (e.g., partially polarized). That is, the wafer scattered light can be unpolarized in certain portions of the pupil plane. In a specific example, unpolarized light may result from a relative rough surface, such as 10-20 nm or higher relative to a 266 nm wavelength for incidence light (as compared with less than 0.1 or 1 nm for a smooth surface). The wafer scattered light will tend to be linear or elliptical/circular scattered as a function of scattering angle. Said in another way, an incident beam can impinge at different angles with respect to the peaks and valleys in the surface topography and result in the scattered light constructively interfering for certain angles to result in linear or elliptical/circular polarized wafer scattering. Conversely, the scattered wafer light destructively interferes at other angles so that it becomes unpolarized. Accordingly, different portions of unpolarized light, which is difficult to fully extinguish, can be partially blocked by the aperture mask 710.

The configurable waveplate 712a and linear polarizer 712b are positioned relative to one another and together forms the analyzer subsystem 712. Optionally, any waveplate may be utilized and is configured for adjusting a phase difference for the collected scattered light's electric field components. Both the ¼ waveplate 712a and linear polarizer 712b may be insertable into the optical path. The ¼ waveplate 712a serves to produce linear polarized light from elliptical/circular polarized light, such as wafer scattering, while simultaneously modulating the polarization status of particle/defect scattering. The linear polarizer 712b extends the output beam's polarization in a particular direction. If the linear polarizer 712b is aligned perpendicularly to the linearized polarization direction of the wafer scattering, the wafer scattering will be fully extinguished or at least reduced to undetectable or minimally detectable levels so that SNR is maximized.

In addition, relay lens 714 and FP lens 716 together image the pupil or aperture mask onto the image sensor 718. The sensor 718 only captures the aperture mask image when the FP relay lens 716 is inserted into the optical path. In this example, the image sensor 718 captures a full size pupil image, instead of the wafer image, when the aperture mask is fully open (AM1), where x' (NAx) and y' (NAy) are pupil coordinates.

Figure 10:
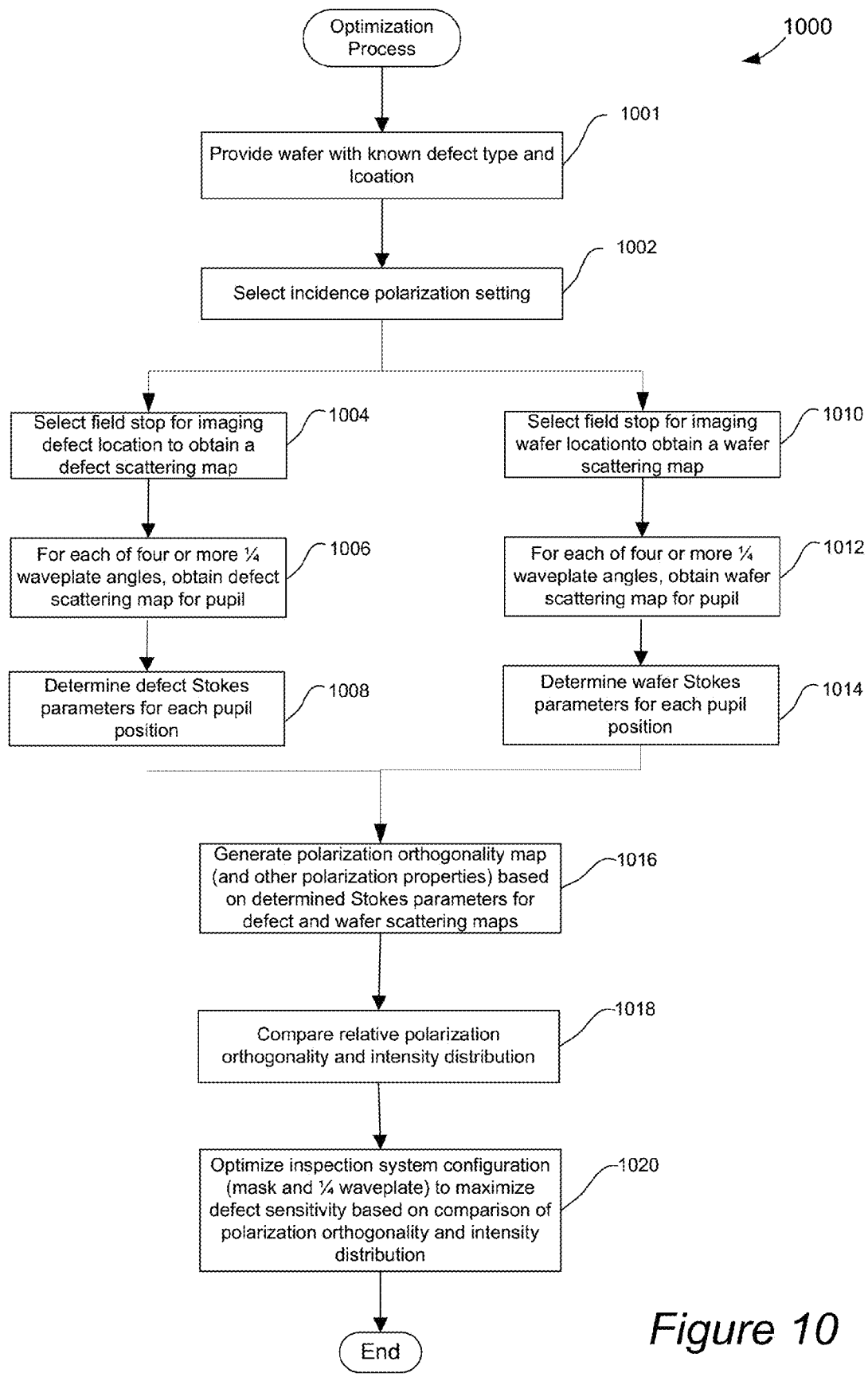
FIG. 10 is a flow chart illustrating an optimization process in accordance with a specific implementation of the present invention.

In general, the Stokes equations may be used to optimize the tool settings as further described herein. Any suitable process for optimizing the polarization and aperture settings of an optical tool may be utilized. FIG. 10 is a flow chart illustrating an optimization process 1000 in accordance with a specific implementation of the present invention. Initially, a wafer with a known defect type and location is provided in operation 1001. For instance, a defect formed from a selected material is deposited on a bare wafer surface. A wafer may include known defects of various sizes and types, which have been formed at specific locations. Each defect may also be, for example, imaged with a high-resolution tool, such as a scanning electron microscope, to locate such defect's location. After the defect locations are determined, the wafer, along with defect locations, may then be loaded onto a stage of an optical tool, and such stage can be moved relative to the optical tool's illumination column so that the defect will be imaged.

An incidence polarization may then be selected in operation 1002. For instance, a polarization setting may be initially selected (or adjusted) via a second ½ waveplate 702d on the illumination side (e.g., FIG. 7). Various settings may be tried for the process 1000 below so as to find optimal settings for maximized defect sensitivity.

To enable localized characterization for a region of interest on wafers, different field stops may be applied to obviate the light scattered from unwanted areas inside the sensor's field of view. In an example in which wafers have small array regions surrounded by page breaks or logic areas, a cropped field stop may be employed such as FS2 or FS3 illustrated in FIG. 9A. In an extreme case, the size of the field stop may be further reduced to enclose only a single defect of interest, such as FS4. However, this last setting requires the wafer scattering to be much lower compared to defect scattering, such as a relatively large particle deposited on smooth bare silicon surface, so that the measured scattering map will represent mostly the signal coming from the defect and not the wafer.

Thus, a field stop for imaging the defect location may be selected to obtain a defect scattering map in operation 1004. For instance, the field stop FS4 (see FIG. 9A) may be selected to position over the defect's known position, excluding the surrounding wafer surface. For each of four or more (N≥4) ¼ waveplate angles β, a defect scattering map may then be obtained in operation 1006. That is, the reflected and scattered intensity for each pixel of the imaged pupil or pupil plane is obtained (e.g., as imaged on sensor 718).

The defect Stokes parameters for each pupil position may then be determined in operation 1008. Assuming the linear polarizer 712b is aligned along x' direction and the ¼ waveplate rotation angle is β, the pupil image is related to the four elements of the Stokes vector by the following equation:

$$I(x', y') = \frac{1}{2}S_0(x', y') + \frac{1}{4}S_1(x', y') + \frac{1}{4}S_1(x', y')\cos(4\beta) + \frac{1}{4}S_2(x', y')\sin(4\beta) + \frac{1}{2}S_3(x', y')\sin(2\beta) \quad (10)$$

The above Equation (10) could be rewritten as follows:

$$y_i = x_0 + a_i x_1 + b_i x_2 + c_i x_3$$

with i=1~N.

where:

$$y_i = I_i(x', y') + \frac{1}{4}S_1(x', y') \quad (11)$$

$$x_0 = \frac{1}{2}S_0(x', y') + \frac{1}{4}S_1(x', y')$$

$$x_1 = \frac{1}{4}S_1(x', y')$$

$$x_2 = \frac{1}{4}S_2(x', y')$$

$$x_3 = \frac{1}{4}S_3(x', y')$$

$$x_4 = \frac{1}{2}S_4(x', y')$$

$$a_i = \cos(4\beta)$$

$$b_i = \sin(4\beta)$$

$$c_i = \sin(2\beta)$$

To solve the Stokes vector as defined in Equation (3) and as shown in Equation (10) and (11), the ¼ waveplate 712a is rotated to N (N≥4) discrete angles β in the range of 0 to 180 degrees, i.e., i=1~N in Equation (11). Additionally, each N pupil image corresponds to a discrete ¼ waveplate angle β. In general, Stokes vectors at each individual pixel may be calculated based on the N pupil images. For example, four different measurements at the four different angles may be obtained to solve for four unknowns: $S_0$-$S_3$. The output of scatterometry measurements is a four-elements Stokes vector for each pixel of the pupil image, with each element of Stokes vector in the form of a 2-D matrix:

$$\Rightarrow \begin{cases} S_0(x', y') = 2x_0 - 2x_1 \\ S_1(x', y') = 4x_1 \\ S_2(x', y') = 4x_2 \\ S_3(x', y') = 2x_3 \end{cases} \quad (12)$$

A similar imaging and Stokes calculation process may be performed for the wafer region (non-defect or bare wafer area) in parallel or sequentially with the defect process. For instance, the field stop for imaging the wafer region may be selected to obtain a wafer scattering map in operation 1010. For instance, a larger field stop, such as FS2, may be positioned over a wafer region. For each of four or more (N≥4) ¼ waveplate angles, a wafer scattering map may be obtained for the pupil in operation 1012. The wafer Stokes parameters for each pupil position may then be determined in operation 1014.

A polarization orthogonality map may then be generated based on the determined Stokes parameters for the defect and wafer scattering maps in operation 1016. Other polarization or light properties may also be determined in operation 1016. Knowing the four elements of Stokes vector for each wafer and particle position as shown in Equation (12), polarization properties of the combined scattered light may then be extracted, including the polarized light intensity distribution Spol (Equation 4), the phase of polarized light δ (Equation 8), and the degree of polarization p (Equation 6). Together with the first element of Stokes vector $S_0$ representing the total scattering intensity distribution of scattering maps, the scatterotnetry measurements can be used to unveil a full picture of how wafer scattering is distributed, polarized, and depolarized at the pupil of the microscope objective. This full picture can be used to select optimal tool configuration for maximizing defect sensitivity.

The relative polarization orthogonality and intensity distribution may then be compared in operation 1018. The inspection system configuration may then be optimized to maximize defect sensitivity based on relative comparison of polarization orthogonality and intensity distribution in operation 1020, and the process 1000 ends. The analyzer setting will be most effective within the pupil space in which polarization orthogonality is as high as possible, while mask optimization makes efficient use of scattering intensity distribution. The specifically configured system may then be used to locate unknown defects on a wafer using any suitable inspection process, such as comparing to known defect scattering signatures, a reference image obtained from an identical die or cell, or a rendered reference image.

By appropriately weighting one factor over another, such as relative defect intensity and polarization orthogonality, the optimization process shall ultimately lead to a preferable combination of configurable variables of the optical system to obtain a maximized defect sensitivity. That is, light from the wafer surface is blocked as much as possible, while blocking only a minimal amount of defect light. For instance, the wafer signal may be elliptical, while the particle signal is not elliptical. In this example, elliptical light can be blocked. A ¼ waveplate in the collection path (e.g., 712a) can be positioned and rotated to convert circularly or elliptically polarized wafer light into linear polarized wafer light, which can then be blocked with an analyzer (e.g., linear polarizer 712b).

The above optimization process may then be repeated for different illumination polarization settings. If the results of the measurements and determined polarization parameters were represented by the example of FIG. 4, by way of example, an incident linear polarization of L45 has a better defect sensitivity, as compared to either pure S or P illumination polarization. In addition, a mask applied towards the bottom half of the pupil (encircled by the thick dotted line 402) could further enhance defect sensitivity.

Figure 11:
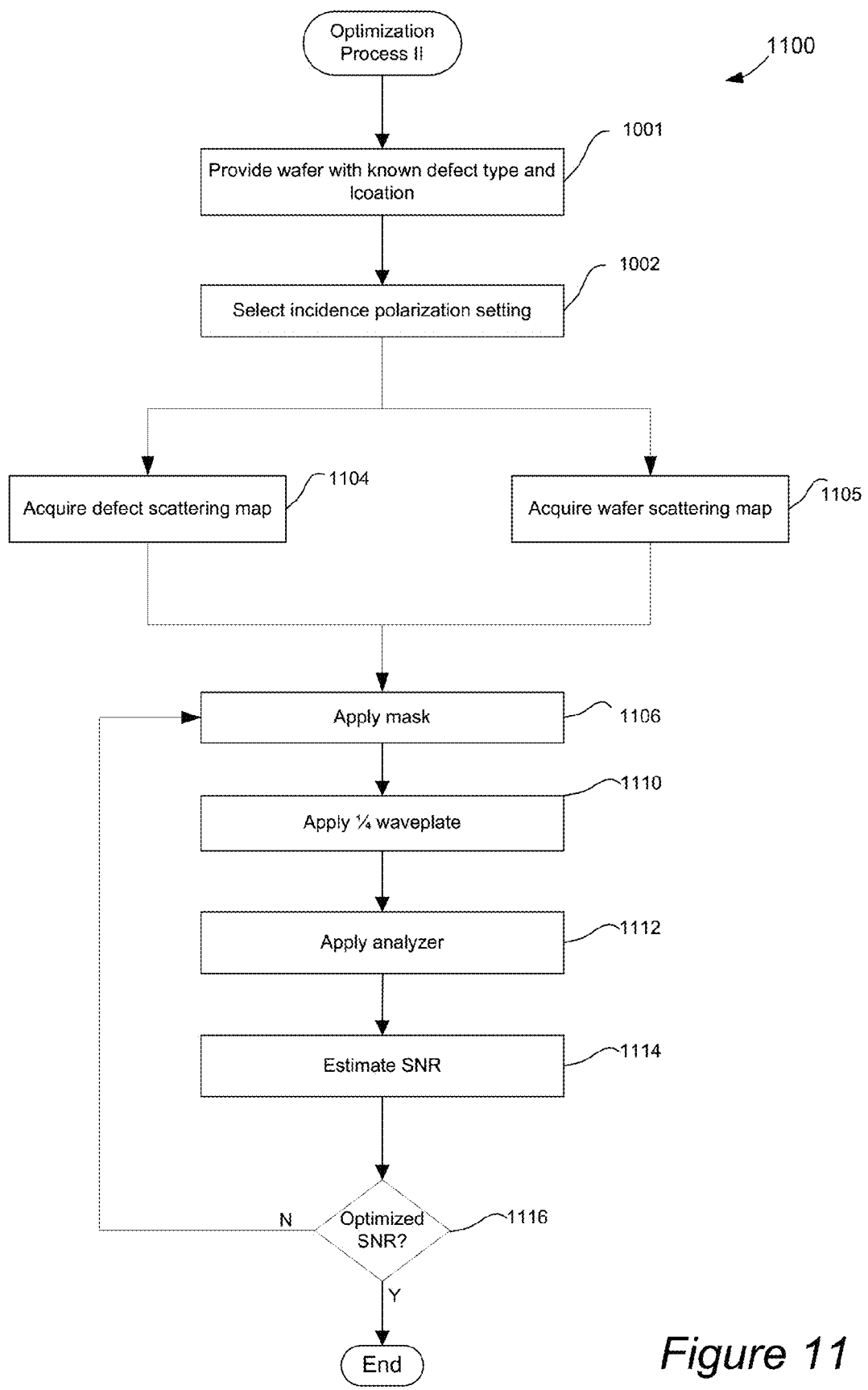
FIG. 11 is a flow chart illustrating an optimization process in accordance with an alternative embodiment of the present invention.

Alternatively, an optimization process 1100 may be performed offline in an iterative manner as illustrated in FIG. 11. Similar to the process 1000 of FIG. 10, a wafer with a known defect type and location is provided in operation 1001 and an incidence polarization is selected in operation 1002. A defect scattering map (1104) and wafer scattering map (1105) may be obtained. The defect and wafer scattering maps may be obtained by imaging with a full-size aperture (AM1).

Instead of imaging at different selected physical VI waveplate and analyzer settings on the tool itself, an aperture mask, a ¼ waveplate, and an analyzer could be applied mimetically to both defect and wafer scattering maps in operations 1106, 1110, and 1112, respectively. The SNR may then be estimated based on the adjusted defect and wafer scattering maps in operation 1114. It may then be determined whether the estimated SNR is optimized in operation 1116. For example, the aperture mask, ¼ waveplate, and analyzer may be configured in various combinations until a maximized SNR is reached and the process 1100 ends.

In certain embodiments, a ¼ waveplate is applied ahead of applying the linear analyzer. This configuration can be beneficial in the case in which wafer scattering is elliptically or circularly polarized, which a ¼ waveplate could convert it into linearly polarized light and, hence, be fully extinguished by the linear analyzer.

Figure 12:
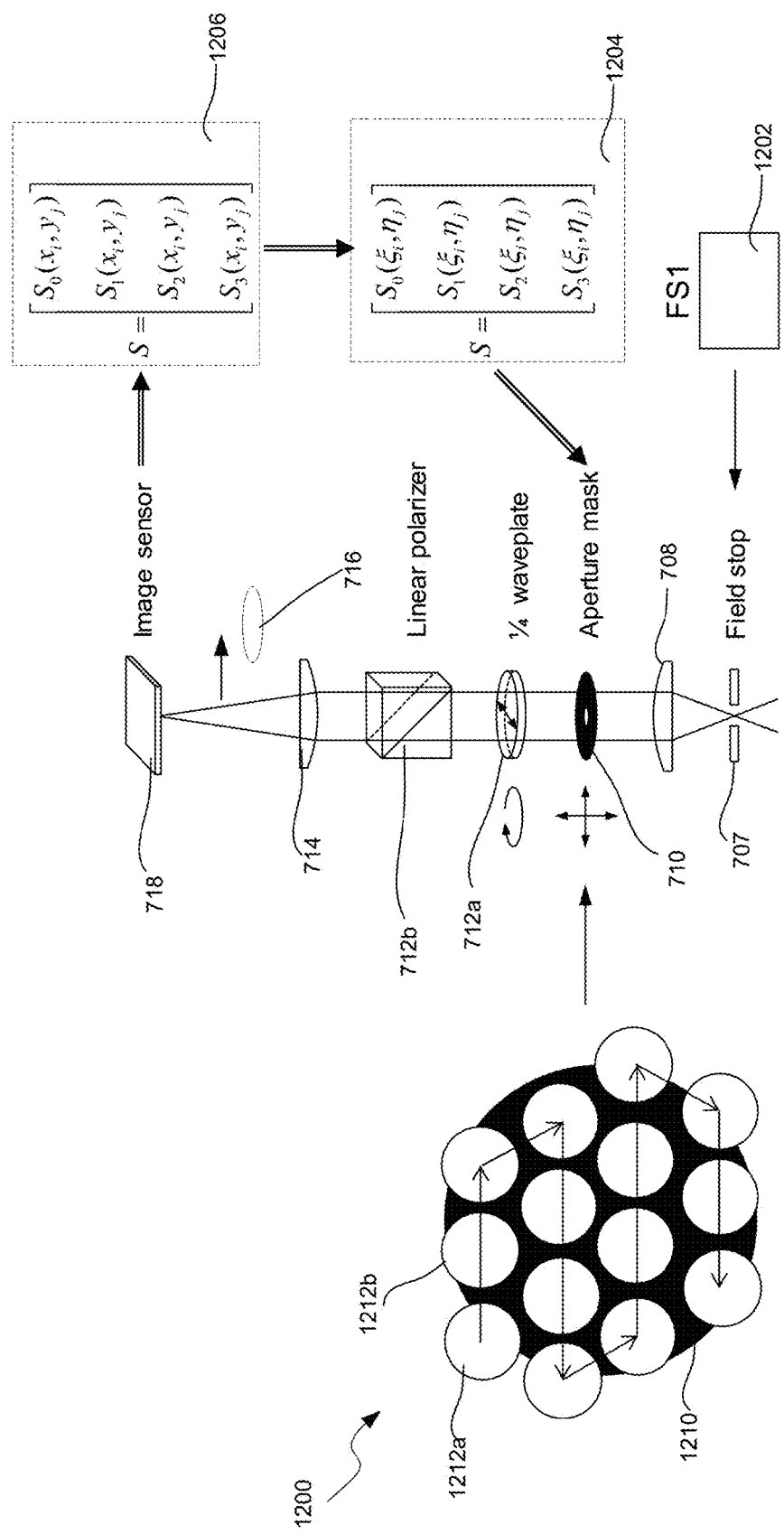
FIG. 12 is a diagrammatic representation of an inspection system in accordance with an alternative embodiment of the present invention.

There may be two disadvantages with directly characterizing defect scattering at the pupil plane. First, it may sometimes be difficult to separate defect and wafer scattering at the pupil space. Secondly, an excessively small field stop FS4 may adversely impact the speckle noise of the pupil image. In an alternative implementation as shown in FIG. 12, system 1200 may include a translatable small size aperture mask 1210 together with a full size field stop FS1 1202. In addition, the FP relay lens 716 may be removed so that image sensor 718 captures the defect image, instead of the pupil image.

Stokes vectors (1206) of the defect pixels may then be calculated at each aperture mask XY position (e.g., 1212a and 1212b). Finally, a full scattering map (1204) of the defect at the pupil plane may be reconstructed by interpolation of Stokes vectors (1206) captured on wafer images. In other words, Stokes vector (1204) at the pupil plane may be discretely sampled by successively translating the aperture mask (1212a, 1212b, . . . ) across the entire aperture and then fused from multiple Stokes vectors captured at the image plane (1206).

Along with the above described techniques and systems, any suitable number and type of techniques may be implemented to improve the dynamic range of the scatterometry measurements. For example, the illumination subsystem may be configured to modulate the incident power from 100% to below 0.1%. Secondly, the exposure time of the image sensor may be adjusted from about a microsecond to about a second level. Moreover, neutral density filters may be inserted at the pupil plane to further increase dynamic range. The overall dynamic range, therefore, could well exceed $10^8$, which would be particularly beneficial for characterizing wafers with strong specular reflection or non-zero order diffractions.

Figure 13:
FIG. 13 represents one possible step by step optimization for a 48.5 nm SiO2 particle deposited on a W film wafer in accordance with a specific application of the present invention.

Defect sensitivity improvements may be observed for a number of opaque rough film wafers as well as on pattern wafers. FIG. 13 represents one possible step by step optimization for a 48.5 nm SiO2 particle deposited on a W film wafer in accordance with a specific application of the present invention. The starting point is S illumination with unpolarized full aperture collection. This setting has conventionally been adopted as an optimal mode for detecting medium size particles on rougher films. The baseline SN (signal to noise) value is 16.99. In the second column, illumination polarization is changed from pure S (L90) to L56 while leaving the collection optics unchanged. An L56 polarization state means that the illumination source is still linearly polarized but the E field is rotated 56-deg off the plane of incidence. In this case, the SN value has dropped to 9.48. Further in the third column, a vertically oriented ¼ waveplate and a 70-deg linear polarizer are applied in sequence in the imaging chain. An instant result of this change is that the bottom part of the pupil plane becomes darker indicating wafer scattering is significantly suppressed therein. Finally, an aperture mask is applied to the bottom half of the pupil plane. The resulting optimized SN value is 46.57, which represent about a 2.7× improvement versus the baseline S illumination with unpolarized full aperture collection.

It has been found that as illumination changes from S (L90) to L56, the particle signal drops, contributing to a reduction of SN from 16.99 to 9.48. However, polarization orthogonality increases simultaneously as illumination polarization changes from S to P. When a ¼ waveplate is applied, the polarization state on part of the wafer scattering is converted to linear polarization, which can then be fully extinguished by a linear polarizer. Finally, when an aperture mask that only covers the optimized low haze region of the pupil is applied, the particle SN is significantly improved, as compared to pure S polarization illumination.

Figure 14:
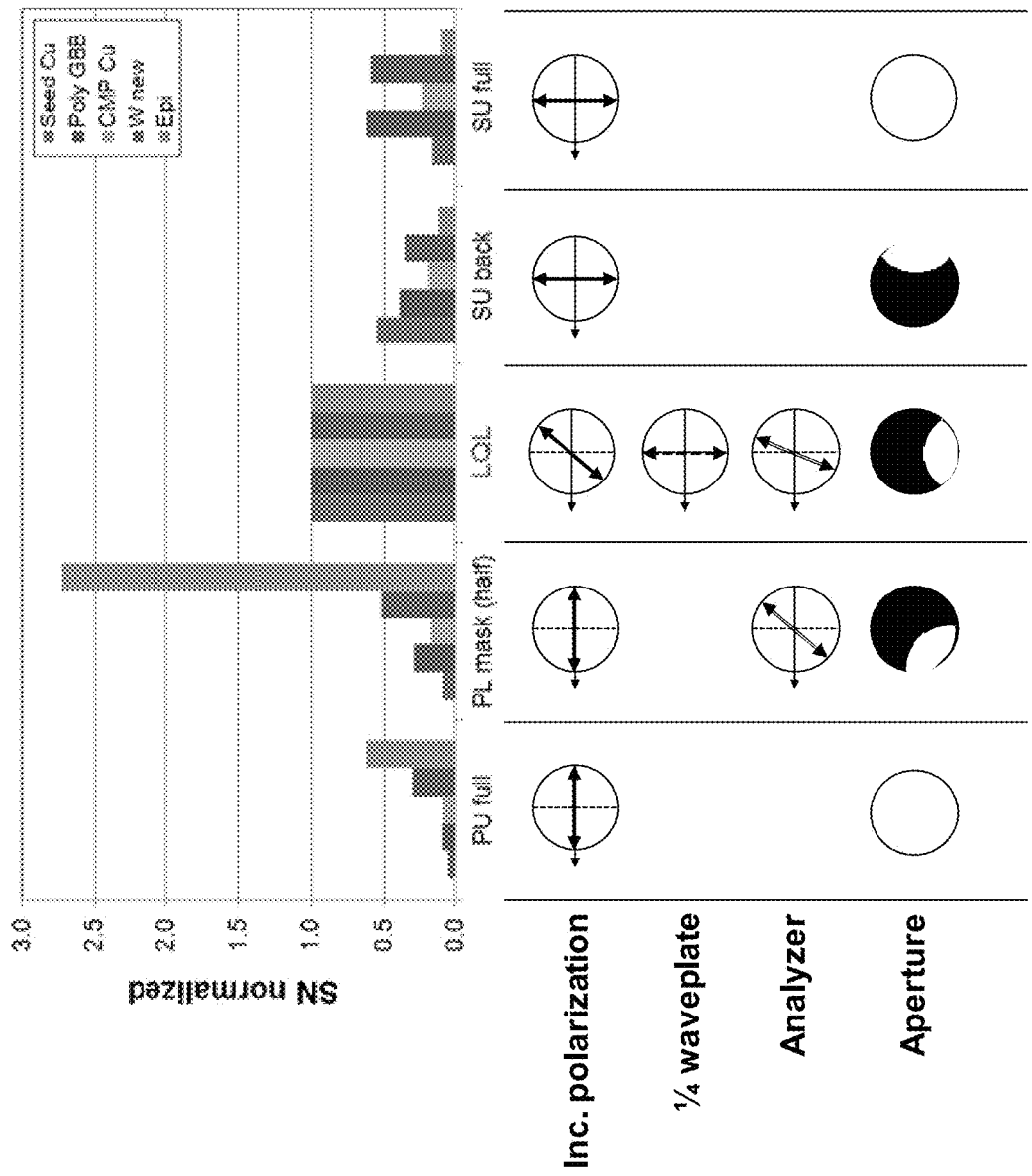
FIG. 14 is a bar chart of SN values of deposited SiO2 particles on five different wafers and under five imaging modes.

Experimental results show a particle sensitivity improvement that is consistent among a few rough film wafers, including seed Cu, poly, CMP Cu, and W. Shown in FIG. 14 is a bar chart of SN values of deposited SiO2 particles under five imaging modes: (1) PU full: P polarization illumination with unpolarized full aperture collection, (2) PL mask (half): P polarization illumination with optimal linear analyzer and mask, (3) LQL: arbitrary linear polarization illumination with ¼ waveplate and optimal linear analyzer and mask, (4) SU back: S polarization illumination with unpolarized backward collection, and (5) SU full: S polarization illumination with unpolarized full collection.

All SN values are normalized with respect to LQL mode for easier comparison. For relatively rougher films (seed Cu, poly, CMP Cu, and W), the optimal mode appears to be LQL with an intermediate illumination polarization state between P and S, consistent with simulations shown in FIG. 4. The SN improvement ratio ranges from 1.6× (poly with strong depolarization) to 4× (CMP Cu with less depolarization), compared to the best of conventional baseline mode. For a relatively smooth Epi wafer, however, the optimal mode appears to be PL mask (half), in agreement with simulations shown in FIG. 5. The reason may be that for small size particles on smooth surface, the particle signal under P illumination is stronger than under S illumination. In addition, the particle scattering polarization is crossed with wafer scattering. Therefore, it may be predicted that as the optimization process keeps being implemented for smaller and smaller particles on smooth film, the mode will eventually converge to the PL mask mode where P polarization is preferred over other polarization states.

Figure 15:
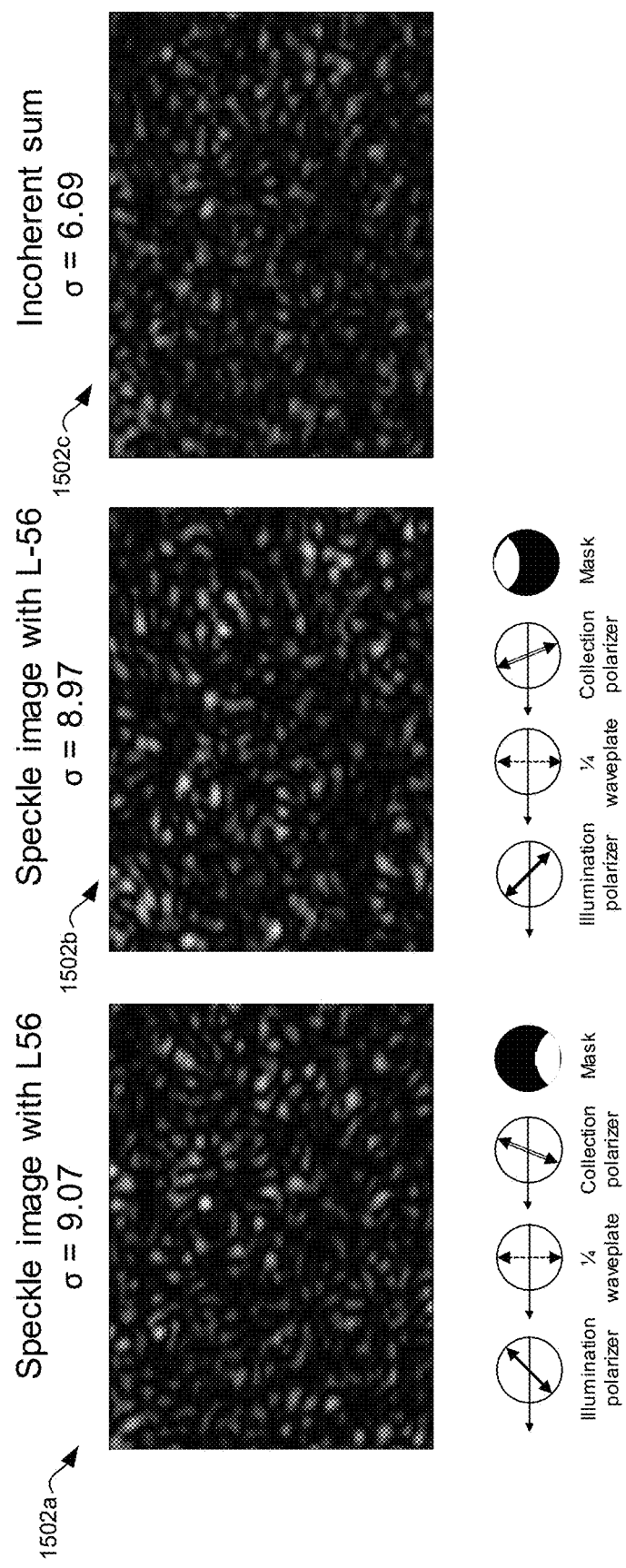
FIG. 15 represents an improvement using two sequential scans with different linear incidence polarizations in accordance with one example implementation.

The particle sensitivity may also be further improved by two sequential scans with different linear incidence polarizations. As shown in FIG. 15, the first scan 1502a adopted the same settings of illumination polarization and collection optics as shown in FIG. 13. In the second scan 1502b, illumination polarization is rotated to the opposite direction with respect to the plane of incidence, noted as L-56; collection analyzer is correspondingly changed to 110-deg; and aperture mask is moved to the upper portion of pupil. Since the aperture masks of two scans take two different regions of the pupil space, their speckle noises are uncorrelated. The defect images could be added incoherently with an additional ~1.4× reduction ratio of wafer noise as shown by incoherent summed image 1502c. However, it is worth noting that this technique requires defect responsivity to be consistent with two symmetric linear incidence polarization angles, so that defect signal will not be dropped by the incoherent sum of two images.

Figure 16:
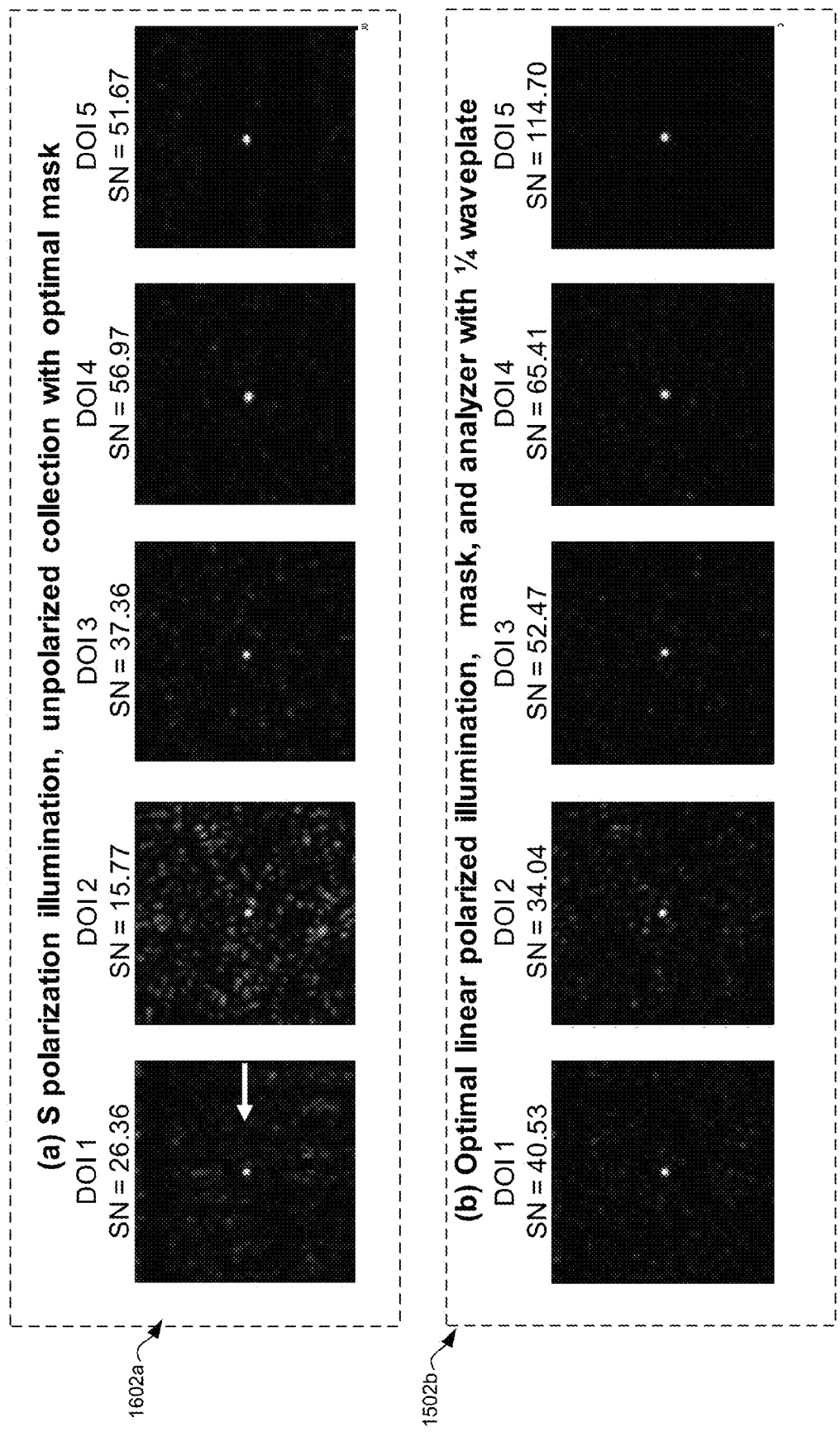
FIG. 16 illustrates images of protrusion defects that are taken under conventional S polarization illumination with unpolarized optimal collection masks and under optimal linear polarized illumination with optimized waveplate, analyzer and collection masks.

Sensitivity improvement is further shown on pattern wafers with line space structures and protrusion defects. Shown in FIG. 16 are images 1602a of protrusion DOI (Defect of Interest) that are taken under conventional S polarization illumination with unpolarized optimal collection masks. The white arrow in the first image (top-left) indicates the illumination azimuth direction which is also the direction of line patterns. Corresponding defect images 1602b with optimized linear incidence polarization, collection aperture, ¼ waveplate, and analyzer are shown. On average the SN improvement ratio is 1.7× compared to baseline S polarization illumination.

Figure 17:
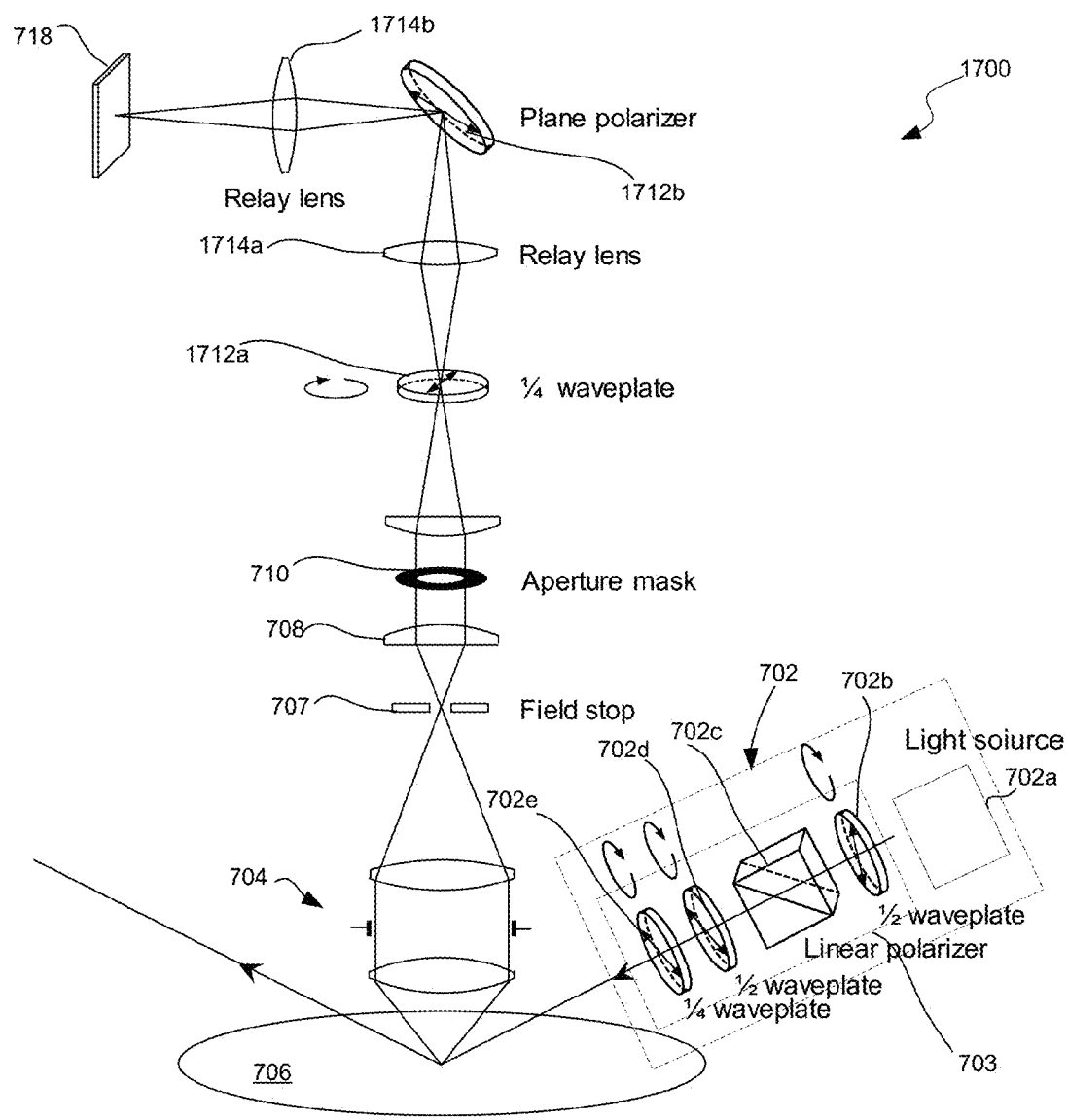
FIG. 17 illustrates an alternative embodiment of an inspection apparatus in which a ¼ waveplate and linear polarizer are sequentially positioned in the collection path at two conjugate field planes.

FIG. 17 illustrates an alternative embodiment of an inspection apparatus 1700. The microscope objective, illumination subsystem, and collection aperture mask are the same as in FIG. 7. In the collection path however the ¼ waveplate 1712a and linear polarizer 1712b are sequentially positioned at two conjugate field planes. The system also includes relay lens 1714a and 1714b for relaying such image towards the sensor 718. Consequently, either analyzing or modulation of the polarization status of scattered light is realized at an intermediate image plane, instead of at the pupil plane.

Figure 18:
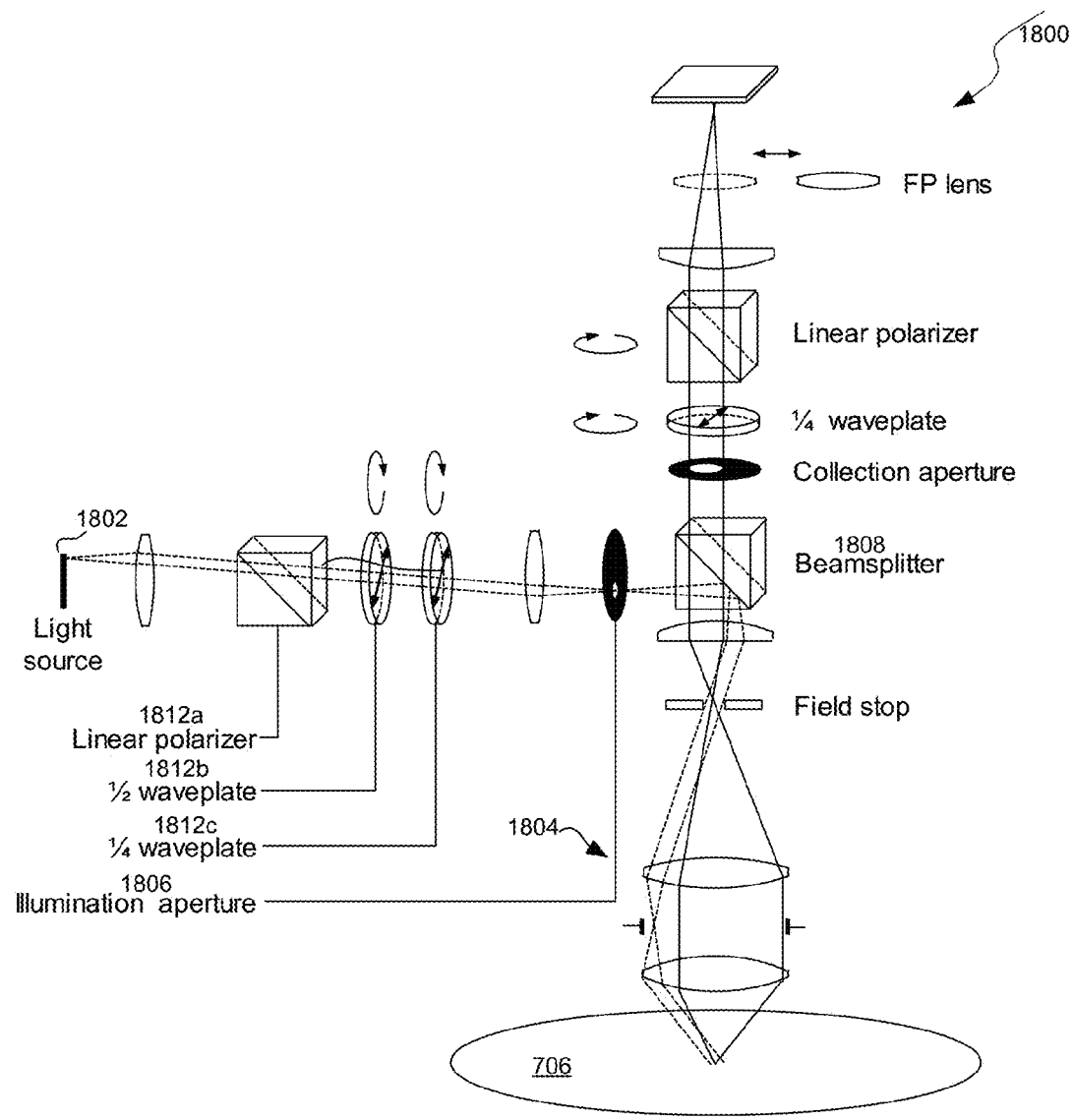
FIG. 18 illustrates an alternative embodiment of an inspection system that utilizes a broadband source.

In another alternative embodiment, a bright field type microscope objective may be implemented. As shown in FIG. 18, instead of illuminating the wafer from outside of the objective lens using a narrowband light source such as a laser, a broadband source 1802a, such as a lamp or LED, illuminates the wafer through the microscope objective 1804. To enable flexible control of illumination polarization states, similarly along the illumination path are positioned a linear polarizer 1812a, a ½ waveplate 1812b to rotate the linear polarization angle, and a ¼ waveplate 1812c to modulate the degree of elliptical polarization. An illumination aperture 1806 is applied to spatially filter the illumination source so that the collection path may be customized as DF imaging mode. The illumination path and collection path are separated by a beamsplitter 1808. In the collection path following the beamsplitter 1808, similar optical elements as shown in FIG. 7 are arranged. This embodiment shows that flexible illumination polarization control and optimization may be carried out on most existing BF wafer inspection tools as on those of inspection tools.

Certain embodiments of the present invention provide optimization of illumination polarization at arbitrary polarization states, besides S and P. In other words, the system improves defect sensitivity by modulating illumination polarization between P and S and balancing between a scattering intensity factor and a polarization orthogonality factor. This flexible design inherently provides a new degree of freedom of optimization that rarely has been attempted in prior arts. Additionally, a ¼ waveplate along with an optimized analyzer maximizes suppression of wafer noise in cases in which it is either elliptically or circularly polarized. Compared to techniques for reducing wafer noise using only the analyzer, certain embodiments provide a more effective noise suppression solution and, hence, possibly leading to much better sensitivity. Experimental results have demonstrated 1.6× to 4× SN improvement of deposited SiO2 particles on opaque rough film wafers. While on line pattern wafer with protrusion DOIs, on average 1.7× SN improvement is achieved in comparison with baseline S polarization illumination.

Two sequential scans with opposite linear polarization angles of the illumination source may also be applied. Due to symmetry, the optimal collection masks of the two scans generally cover different portions of the imaging pupil. As a result, the cross correlation of the background speckle of two scans are likely very low In turn ~1.4× further reduction of speckle noise could be achieved by incoherently addition of the defect image of two scans.

Certain embodiments of the present invention enable polarimetric scatterometery characterization of scattered light of both defects and waters. The measurements described herein can be used to unveil important characteristics about wafer scattering, including scattering intensity distribution, intensity of polarized scattered light, phase of polarized scattered light, and degree of polarization. This information can then be used either for defect sensitivity optimization or for defect classification, such as using phase and degree of polarization on individual defect pixels.

Other applications can provide SN improvement of defects on rough film wafers and array patterned wafers. An optimum illumination polarization angle (wrt incident plane) that provides better SN for rough films, when combined with phase retardation compensation and analyzer. Use of a ¼ waveplate together with an optimal analyzer can maximize suppression of wafer noise. Polarimetric scatterometry mapping capability may also be provided on both defect and wafer scattering. Additionally, defect classification capability can be accomplished using phase or degree of polarization information of scattered light. The techniques and systems described herein can be combined with structured illumination to further improve sensitivity. The techniques and systems described herein can also be combined with solid or liquid immersion to further improve sensitivity.

Regardless of the particular system embodiment, each optical element may be optimized for the particular wavelength range of the light in the path of such optical element. Optimization may include minimizing wavelength-dependent aberrations, for example, by selection of glass type, arrangement, shapes, and coatings (e.g., anti-reflective coatings, highly reflective coatings) for minimizing aberrations for the corresponding wavelength range. For example, the lenses are arranged to minimize the effects caused by dispersion by shorter or longer wavelength ranges. In another embodiment, all the optical elements are reflective. Examples of reflective inspection systems and configurations are further described in U.S. Pat. No. 7,351,980 issued 1 Apr. 2008, which is incorporated herein by reference in its entirety.

The optical layout of the inspection tool can vary from that described above. For example, the system microscope objective lens can be one of many possible layouts, as long as the transmission coatings are optimized for the particular selected wavelength band or sub-band and the aberration over each waveband is minimized. Different light sources can be used for each path. For instance, a Xe source may be used for the long wavelength path and an HgXe or Hg lamp may be used for the short wavelength path. Multiple LED or speckle buster laser diodes are also possible sources for each path. The zoom ratio can be modified to include different magnification ranges either via a lens-only approach, a mostly fixed lens with an optical trombone, or any combination thereof.

As illustrated above, the sample may also be placed on a stage of the inspection system, and the inspection system may also include a positioning mechanism for moving the stage (and sample) relative to the incident beam. By way of examples, one or more motor mechanisms may each be formed from a screw drive and stepper motor, linear drive with feedback position, or band actuator and stepper motor. The one or more positioning mechanisms may also be configured to move other components of the inspection system, such as illumination or collection mirrors, apertures, FP relay lens, wavelength filters, polarizers, analyzers, waveplates, etc.

It should be noted that the above description and drawings of an inspection system are not to be construed as a limitation on the specific components of the system and that the system may be embodied in many other forms. For example, it is contemplated that the inspection or measurement tool may have any suitable features from any number of known imaging or metrology tools arranged for detecting defects and/or resolving the critical aspects of features of a reticle or wafer. By way of example, an inspection or measurement tool may be adapted for bright field imaging microscopy, dark field imaging microscopy, full sky imaging microscopy, phase contrast microscopy, polarization contrast microscopy, and coherence probe microscopy. It is also contemplated that single and multiple image methods may be used in order to capture images of the target. These methods include, for example, single grab, double grab, single grab coherence probe microscopy (CPM) and double grab CPM methods. Non-imaging optical methods, such as scatterometry, may also be contemplated as forming part of the inspection or metrology apparatus.

Any suitable lens arrangement may be used to direct the incident beam towards the sample and direct the output beam emanating from the sample towards a detector. The illumination and collection optical elements of the system may be reflective or transmissive. The output beam may be reflected or scattered from the sample or transmitted through the sample. Likewise, any suitable detector type or number of detection elements may be used to receive the output beam and provide an image or a signal based on the characteristics (e.g., intensity) of the received output beam.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. For example, the defect detection characteristic data may be obtained from a transmitted, reflected, or a combination output beam. Accordingly, the present embodiments are to be considered as illustrative and not restrictive, and the invention is not to be limited to the details given herein.

What is claimed is:

1. An inspection system for inspecting a semiconductor sample, comprising:
   an illumination optics subsystem for generating and directing an incident beam towards a defect on a surface of a wafer, wherein the illumination optics subsystem includes a light source for generating the incident beam and one or more polarization components for adjusting a ratio and/or a phase difference for the incident beam's electric field components;
   a collection optics subsystem for collecting scattered light from the defect and/or surface in response to the incident beam, wherein the collection optics subsystem comprises an adjustable aperture at the pupil plane, followed by a rotatable waveplate for adjusting a phase difference of electric field components of the collected scattered light, followed by a rotatable analyzer; and
   a controller that is configured to perform the following operations:
      selecting a polarization of the incident beam;
      obtaining a defect scattering map;
      obtaining a surface scattering map; and
      determining a configuration of the one or more polarization components, aperture mask, and rotatable waveplate, and analyzer based on analysis of the defect and surface scattering maps so as to maximize a defect signal to noise ratio.

2. The system of claim 1, wherein the defect and surface maps are obtained at four or more angles of the waveplate of the collection optics subsystem, and wherein determining a configuration is accomplished by:
   for each pupil position at the pupil plane, determining defect Stokes parameters based on the obtained defect scattering map,
   for each pupil position at the pupil plane, determining surface Stokes parameters based on the obtained surface scattering map,
   generating a polarization orthogonality map based on the determined defect and surface Stokes parameters, and
   comparing relative polarization orthogonality values from the polarization orthogonality map and relative intensity distribution values from the defect scattering map to determine the configuration.

3. The system of claim 1, wherein the one or more polarization components of the illumination subsystem include a rotatable ½ waveplate for controlling the incident beam's polarization angle and a rotatable ¼ waveplate for controlling the phase difference of electric field components of incident beam.

4. The system of claim 3, wherein the one or more polarization components of the illumination subsystem further comprise another ½ waveplate and a linear polarizer for controlling the incident beam's power and increasing a dynamic range.

5. The system of claim 4, wherein the ¼ waveplate is positioned before the linear polarizer.

6. The system of claim 1, wherein the collection optics subsystem further includes an adjustable field stop for separately obtaining the defect and surface scattering maps.

7. The system of claim 1, wherein the collection optics subsystem further includes a sensor and one or more relay lens for relaying a pupil image to the sensor.

8. The system of claim 1, wherein the illumination optics subsystem includes an aperture that is open to a full size and determining a configuration is accomplished by iteratively mathematically applying different settings for the aperture mask, ¼ waveplate, and analyzer so as to maximize the defect signal to noise ratio.

9. The system of claim 1, wherein a configuration of the aperture mask is determined so as to block areas of the pupil, except for areas with maximized polarization orthogonality and defect scattering intensity.

10. The system of claim 1, wherein the one or more polarization components of the illumination optics subsystem comprise a linear polarizer, and wherein the rotatable waveplate of the collection optics subsystem is a rotatable ¼ waveplate.

11. The system of claim 10, wherein the linear polarizer and the rotatable ¼ waveplate are each positioned at a conjugate plane.

12. The system of claim 1, wherein the light source is a broadband light source and the illumination optics subsystem is arranged to direct the incident beam through an objective onto the surface of the wafer.

13. A method of inspecting a semiconductor sample, comprising
   in an illumination optics subsystem of an inspection system, generating and directing an incident beam at a selected polarization state towards a defect on a surface of a wafer, wherein the illumination optics subsystem of the inspection system includes a light source for generating the incident beam and one or more polarization components for adjusting a ratio and/or a phase difference for the incident beam's electric field components;
   in a collection optics subsystem of an inspection system, collecting scattered light from the defect and/or surface in response to the incident beam, wherein the collection optics subsystem of the inspection system comprises an adjustable aperture at the pupil plane, followed by a rotatable waveplate for adjusting a phase difference of electric field components of the collected scattered light, followed by a rotatable analyzer;

obtaining a defect scattering map based on the collected scattered light;

obtaining a surface scattering map based on the collected scattered light; and determining a configuration of the one or more polarization components, aperture mask, and rotatable waveplate, and analyzer based on analysis of the defect and surface scattering map so as to maximize a defect signal to noise ratio.

14. The method of claim 13, wherein the defect and surface maps are obtained at four or more angles of the waveplate of the collection optics subsystem, and wherein determining a configuration is accomplished by:

for each pupil position at the pupil plane, determining defect Stokes parameters based on the obtained defect scattering map, for each pupil position at the Pupil plane, determining surface Stokes parameters based on the obtained surface scattering map, generating a polarization orthogonality map based on the determined defect and surface Stokes parameters, and comparing relative polarization orthogonality values from the polarization orthogonality map and relative intensity distribution values from the defect scattering map to determine the configuration.

15. The method of claim 13, wherein the one or more polarization components of the illumination subsystem include a rotatable ½ waveplate for controlling the incident beam's polarization angle and a rotatable ¼ waveplate for controlling the phase difference of the electric field components of the incident beam.

16. The method of claim 15, wherein the ¼ waveplate is positioned before the linear polarizer.

17. The method of claim 13, wherein the collection optics subsystem further includes an adjustable field stop for separately obtaining the defect and surface scattering maps.

18. The method of claim 13, wherein the collection optics subsystem further includes a sensor and one or more relay lens for relaying a pupil image to the sensor.

19. The method of claim 13, wherein the illumination optics subsystem includes an aperture that is open to a full size and determining a configuration is accomplished by iteratively mathematically applying different settings for the aperture mask, ¼ waveplate, and analyzer so as to maximize the defect signal to noise ratio.

20. The method of claim 13, wherein a configuration of the aperture mask is determined so as to block areas of the pupil, except for areas with maximized polarization orthogonality and defect scattering intensity.

21. The method of claim 13, wherein the one or more polarization components of the illumination optics subsystem comprise a linear polarizer, and wherein the rotatable waveplate of the collection optics subsystem is a rotatable ¼ waveplate.

22. The method of claim 13, wherein the light source is a broadband light source and the illumination optics subsystem is arranged to direct the incident beam through an objective onto the surface of the wafer.

* * * * *